(12) United States Patent  
Jongpaiboonkit et al.

(10) Patent No.: US 11,747,269 B2  
(45) Date of Patent: Sep. 5, 2023

(54) SYSTEMS AND METHODS FOR IDENTIFYING A COATING ON AN IMPLANT

(71) Applicant: Warsaw Orthopedic, Inc., Warsaw, IN (US)

(72) Inventors: Leenaporn Jongpaiboonkit, Sterling, MA (US); Peter D. Yurek, North Saint Paul, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/522,569

(22) Filed: Nov. 9, 2021

(65) Prior Publication Data

US 2023/0147097 A1 May 11, 2023

(51) Int. Cl.
| | |
|---|---|
| *G01N 21/31* | (2006.01) |
| *A61F 2/30* | (2006.01) |
| *G01B 11/06* | (2006.01) |
| *G01N 33/483* | (2006.01) |

(52) U.S. Cl.
CPC ......... *G01N 21/31* (2013.01); *A61F 2/30771* (2013.01); *G01B 11/0616* (2013.01); *G01N 33/4833* (2013.01); *A61F 2002/3071* (2013.01); *A61F 2002/3084* (2013.01)

(58) Field of Classification Search
CPC .......... A61F 2/30771; A61F 2002/3071; A61F 2002/3084; G01B 11/0616; G01N 33/4833
USPC ........................................................ 356/319
See application file for complete search history.

(56) References Cited

U.S. PATENT DOCUMENTS

| | | |
|---|---|---|
| 6,736,849 B2 | 5/2004 | Li et al. |
| 6,891,627 B1 | 5/2005 | Levy et al. |
| 6,946,394 B2 | 9/2005 | Fielden et al. |
| 7,580,119 B2 | 8/2009 | Powell et al. |
| 8,007,854 B2 | 8/2011 | Wei et al. |
| 8,335,029 B2 | 12/2012 | Monadgemi |
| 8,893,711 B2 | 11/2014 | Kennedy |
| 9,695,505 B2 | 7/2017 | O'Donoghue et al. |
| 9,839,720 B2 | 12/2017 | Gan et al. |

(Continued)

FOREIGN PATENT DOCUMENTS

| | | | | |
|---|---|---|---|---|
| CN | 102481389 A | * | 5/2012 | ............. A61L 27/34 |
| JP | 2009204313 | * | 9/2009 | |

OTHER PUBLICATIONS

International Search Report and the Written Opinion of the International Searching Authority, European Patent Office, P.B. 5818 Patentlaan 2, NL-2280 HV Rijswijk, International application No. PCT/US2022/045869, dated Feb. 13, 2023.

*Primary Examiner* — Tarifur R Chowdhury
*Assistant Examiner* — Omar H Nixon
(74) *Attorney, Agent, or Firm* — Sorell, Lenna & Schmidt, LLP

(57) ABSTRACT

Systems and methods of identifying a coating on a bone material are provided. The systems and methods comprise providing a bone material and a scanning device; adjusting a distance between the bone material and the scanning device; scanning the bone material using the scanning device; and transmitting a scanned data from the scanning device to a processor configured to analyze the scanned data, and display the analyzed scanned data to identify the coating on the bone material based on the scanned data when the coating meets or fails to meet a predetermined parameter.

18 Claims, 14 Drawing Sheets

(56) References Cited

U.S. PATENT DOCUMENTS

| | | |
|---|---|---|
| 10,173,042 B2 | 1/2019 | Pushpala et al. |
| 2009/0181339 A1* | 7/2009 | Liang .................. A61B 1/24 |
| | | 433/29 |
| 2010/0032572 A1 | 2/2010 | Shelley et al. |
| 2010/0141931 A1* | 6/2010 | Ramirez Mancilla .... G01J 3/50 |
| | | 356/402 |
| 2011/0089348 A1* | 4/2011 | Finarov .................. G01N 21/31 |
| | | 250/559.39 |

* cited by examiner

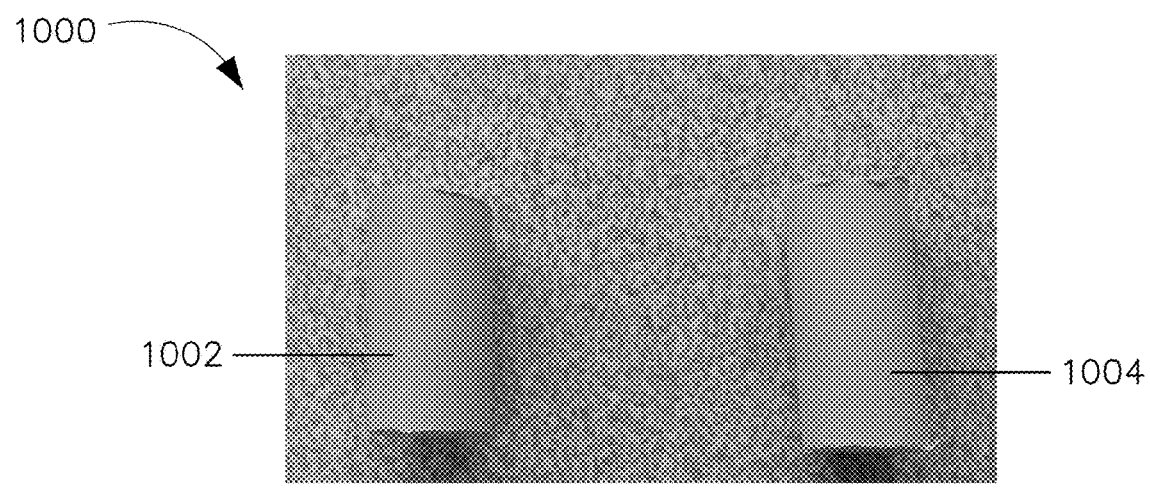
FIG. 18
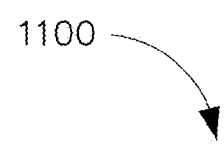
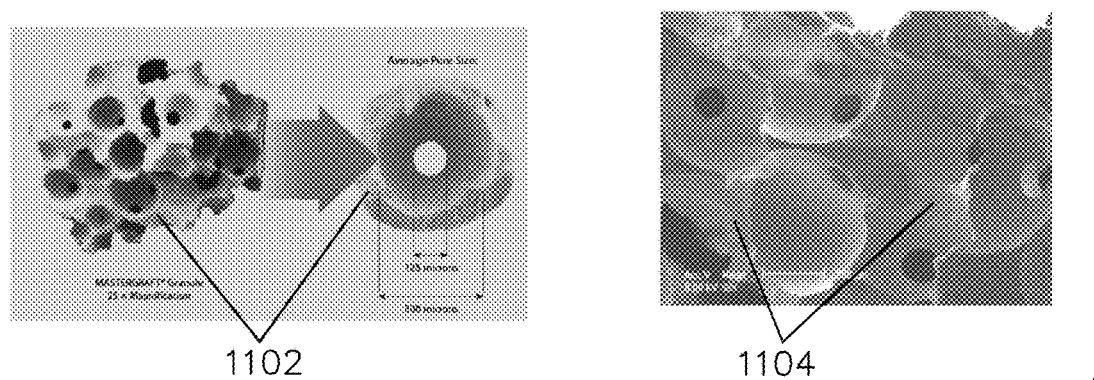
FIG. 19
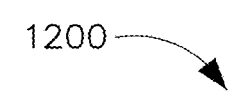
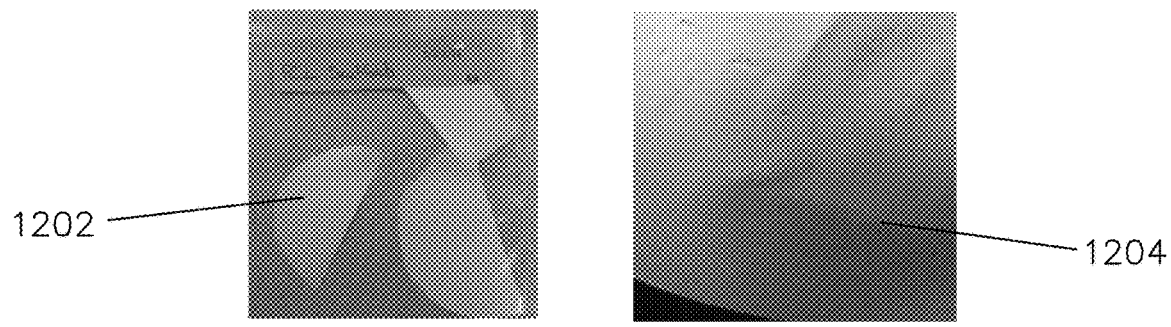
FIG. 20

SYSTEMS AND METHODS FOR IDENTIFYING A COATING ON AN IMPLANT

BACKGROUND

Bone defects or bone voids may be caused by several different factors including, but not limited to trauma, pathological disease, or surgical intervention. Because bone provides both stability and protection to an organism, these defects or voids can be problematic. To address these defects or voids, compositions that contain both natural and synthetic materials have been developed. These compositions may, depending upon the materials contained within them, be used to repair tissues and to impart desirable biological and/or mechanical properties.

Hybrid materials composed of organic polymers coated with inorganic minerals have attracted much attention in biology and medicine due to their combination of advantageous properties. Polymeric materials can be a desirable base material for biomedical applications, as they can be processed into a variety of sizes and geometries and can be designed to bioresorb or bioabsorb in a controllable timeframe. Therefore, polymeric biomaterials have been featured in a variety of applications including medical devices, tissue engineering scaffolds, and drug delivery systems.

Also, calcium phosphate based mineral coatings represent desirable surfaces for biomedical applications, as they can be similar in composition to bone tissue and have been shown to promote favorable interactions with natural bone, a property termed "bioactivity". The surface modification technology associated with mineral coatings seeks to apply an apatite layer with an engineered nanoparticle sized morphology to the surface of a highly porous biphasic calcium phosphate surface. The mineral coated surface has been demonstrated to stimulate bone cells creating an enhanced cellular environment for bone healing. Currently, as the surface technology accomplishes bone stimulation through nanoparticle sized morphology features, the application of nanoparticle sized coatings is indistinguishable to the user. It is a challenge to identify the coating visually on bone material.

Typically, instruments used in identifying and analyzing the coating on bone material include a high-resolution scanning electron microscope (SEM), which produces images of the coating by scanning the surface of the bone material with a focused electron beam. Often times, SEM set up can be time-consuming, involves meticulous sample preparation, additional sample coating steps, and requires more skilled technician time to use and maintain the SEM. When dealing with nanometer coatings and nanometer surface structures, SEM requires high magnification and can only be done in a very selective area.

Therefore, there is a need to have efficient systems and methods for identifying that a particular type of coating (e.g., nanometer coating or nanometer structure), which is no visible to the naked eye, is on bone material in a scalable quantitative way. It would also be beneficial to have a method that reduces processing steps performed to identify the type of coating on bone material including additional sample preparation steps, and additional coating steps for SEM identification while reducing the skilled technician time to use and maintain SEM instruments. It would also be beneficial to automate the coating identification process.

SUMMARY

Systems and methods are provided for identifying a coating (e.g., nanometer coating, nanometer structure, nano- topography, homogeneity, continuity, phase and/or composition) on an implant material (e.g., bone material) that reduces time-consuming steps including meticulous sample preparation, additional sample coating steps, and reduces the skilled technician time. The systems and methods provided allow a user to easily distinguish between uncoated bone material and coated bone material, which cannot be easily done by the naked eye.

In some embodiments, there is a method of identifying a coating on an implant material, the method comprising providing the implant material and a scanning device; adjusting a distance between the implant material and the scanning device; scanning the implant material using the scanning device; and transmitting a scanned data from the scanning device to a processor configured to analyze the scanned data, and display the analyzed scanned data to identify the coating on the implant material based on the scanned data when the coating meets or fails to meet a predetermined parameter.

In some embodiments, there is a method of identifying a coating on a bone material, the method comprising providing the bone material and a scanning device; adjusting a distance between the bone material and the scanning device; scanning the bone material using the scanning device; and transmitting a scanned data from the scanning device to a processor configured to analyze the scanned data, and display the analyzed scanned data to identify the coating on the bone material based on the scanned data when the coating meets or fails to meet a predetermined parameter.

In some embodiments, there is a method of identifying a coating on a bone material, the method comprising providing the bone material having a unique identifier; providing a spectrophotometer; adjusting a distance between the bone material and the spectrophotometer; scanning the bone material using the spectrophotometer; and transmitting a scanned data from the spectrophotometer to a processor configured to analyze the scanned data, and display the analyzed scanned data to identify the coating on the bone material based on the scanned data when the coating meets or fails to meet a predetermined parameter.

In some embodiments, there is a system for identifying a coating on a bone material, the system comprising a scanning device configured to scan the bone material, the scanning device configured to transmit data to a processor, the processor having logic to cause a computer to receive the scanned data, analyze the scanned data and display a coating status of the bone material based on the analyzed data when the coating status meets or fails to meet a predetermined parameter.

In some embodiments, there is a system or method of identifying a coating on a bone material, the system or method comprising providing the bone material and a scanning device; adjusting a distance between the bone material and the scanning device; scanning the bone material using the scanning device; and storing the scanned data and displaying the stored scanned data to identify the coating on the bone material based on the stored scanned data when the coating meets or fails to meet a predetermined parameter.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits, and advantages of the embodiments will be apparent regarding the following description, appended claims and accompanying figures.

FIG. 18 represents one embodiment of a comparison of uncoated bone material and coated bone material.

FIG. 19 represents another embodiment of a comparison of uncoated bone material and coated bone material under SEM micrographs.

FIG. 20 represents another embodiment of a comparison of uncoated bone material and coated bone material.

Figure 1:
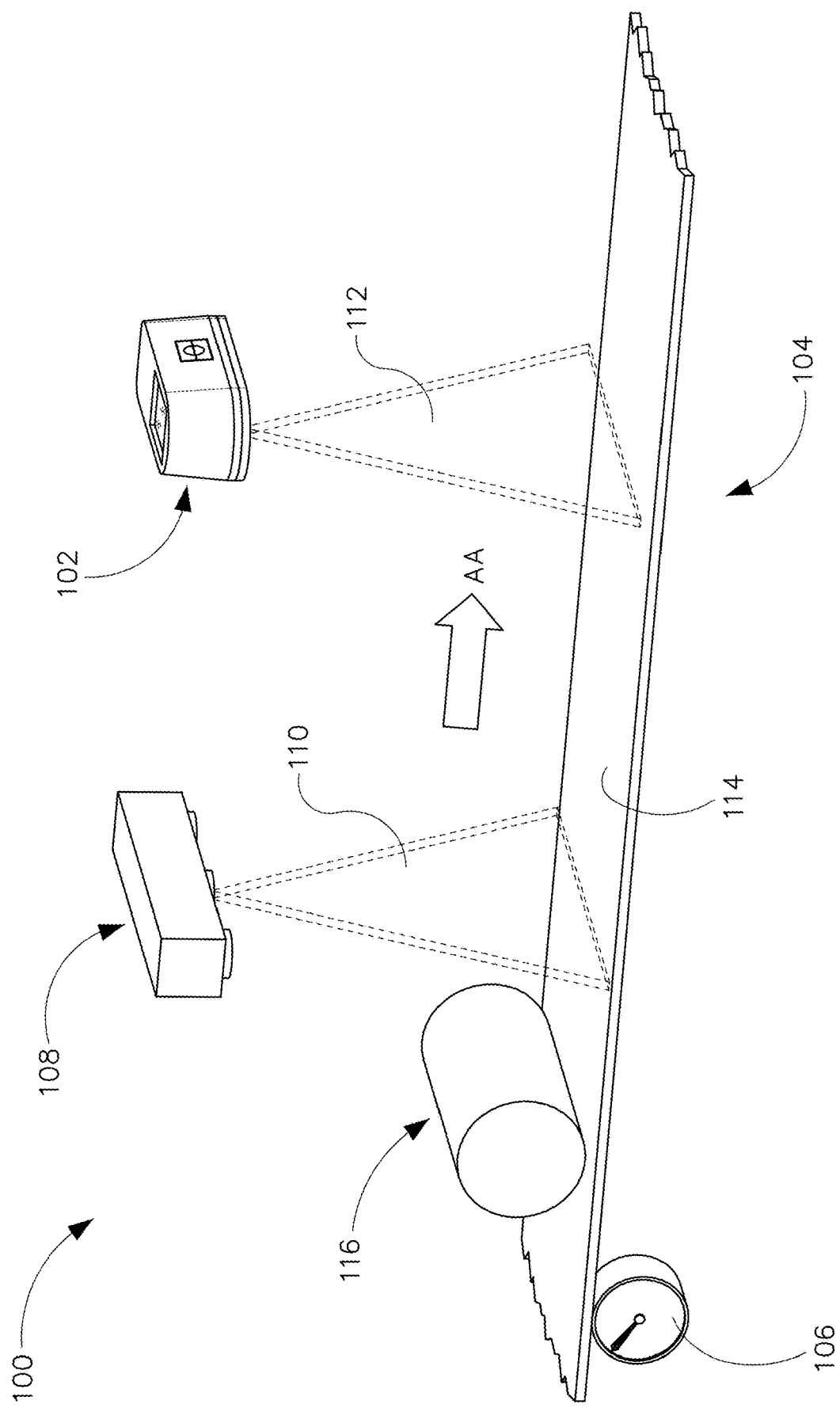
FIG. 1 is a perspective view of one embodiment of a coating identification system, that can be used to quickly detect or identify that a particular type of coating (e.g., nanometer coating or nanometer structure) is on a bone material.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Biocompatible, as used herein, is intended to describe materials that, upon administration in vivo, do not induce undesirable long-term effects.

The term "implant" as utilized herein is intended to refer to any device or material for implantation that aids or augments bone formation or healing. Implants are often applied at a bone defect site, e.g., one resulting from injury, defect brought about during the course of surgery, infection, malignancy or developmental malformation.

Bone, as used herein, refers to bone that is cortical, cancellous, or cortico-cancellous of autogenous, allogenic, xenogeneic, or transgenic origin.

The term "autograft" refers to graft material harvested from the same individual patient who is also recipient of the graft, obtained surgically from non-essential donation sites in the patient.

Bone graft, as used herein, refers to any implant prepared in accordance with the embodiments described herein and therefore may include expressions such as a bone void filler.

The term "nano-sized feature" includes recesses, projections or a combination thereof that are in nanometer size.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteogenic" refers to the ability of a graft material to produce bone independently. To have direct osteogenic activity, the graft must contain cellular components that directly induce bone formation. For example, an allograft seeded with activated MSC s would have the potential to induce bone formation directly, without recruitment and activation of host MSC populations. Because many osteoconductive allografts also can bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals including, without limitation, humans.

The term "implantable" as utilized herein refers to a biocompatible device (e.g., the composition) retaining potential for successful placement within a mammal. The expression "implantable composition" and expressions of the like as utilized herein refer to an object implantable through surgery, injection, or other suitable means whose primary function is achieved either through its physical presence or mechanical properties. An example of the implantable device is the bone material.

The term "moldable" includes that the composition can be shaped by hand or machine or injected into the target tissue site (e.g., bone defect, fracture, or void) into a wide variety of configurations to fit within the bone defect.

The term "cohesive" as used herein means that the composition tends to remain a singular, connected mass upon the addition of fluid, autograft bone or during manipulation, including the exhibition of the ability to be molded or shaped without breaking upon manipulating, or disintegrating or becoming unstable.

The terms "macroparticle" or "macroform" include bone material that is visible to the naked eye. The bone material can be natural bone, synthetic bone material (e.g., demineralized bone, ceramic, etc.) or a combination thereof that is solid or semi-solid before hydration. Typically, the macroparticle can be from 0.01 mm to about 50 mm in length. It is to be understood that the terms macroparticle and macroform can be used interchangeably.

The term "flowable" includes that the composition can be administered in an injectable state via a syringe and/or cannula. The composition is flowable when its consistency is fluid-like and has a viscosity that is lower than that of the viscosity of the composition when in a putty or paste form. Flowable compositions include liquid or fluid (e.g., solution, suspension, or the like) or semi-solid compositions (e.g., gels, cements) that are easy to manipulate and may be brushed, sprayed, dripped, injected, shaped and/or molded at or near the target tissue site. "Flowable" includes compositions with a low viscosity or water-like consistency to those with a high viscosity, such as a paste-like material. In various embodiments, the flowability of the composition allows it to conform to irregularities, crevices, cracks, and/or voids in the bone defect site (e.g., bone void). For example, in various embodiments, the composition may be used to fill one or more voids in an osteolytic lesion.

The term "hydrate," "hydration," "hydratable," "hydrating" or "hydrated" refers to adding an amount of fluid to a composition to increase the amount of moisture content in the composition to form a putty or paste that is flowable.

The term "dehydrated" or "dehydration" refers to a composition that contains a small amount of residual moisture or no moisture content and can be in the form of a dry composition. The dehydrated composition can have a moisture content from about 0 to about 10% based on the total weight of the composition. In some embodiments, when a composition is dehydrated, fluid can be added to the composition to hydrate the composition. A dehydrated composition includes a lyophilized or freeze-dried composition.

The term "bone marrow aspirate" or "BMA" refers to the withdrawal of bone marrow fluid through a syringe and needle to harvest the bone marrow fluid from the patient. Bone marrow aspirate comprises fluid that contains a heterogeneous mix of stem and progenitor cells, platelets, and white blood cells. The bone marrow aspirate can be harvested from various sources in the body including, but not limited to, the iliac crest.

The term "soluble collagen" refers to the solubility of individual tropocollagen molecules in acidic aqueous environments. Tropocollagen may be considered the monomeric unit of collagen fibers and its triple helix structure is well recognized.

"Insoluble collagen" as used herein refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of an animal hide (e. g. bovine, porcine, fish, etc.) that is situated between the grain and the flesh sides.

Identification System and Method

Figure 2:
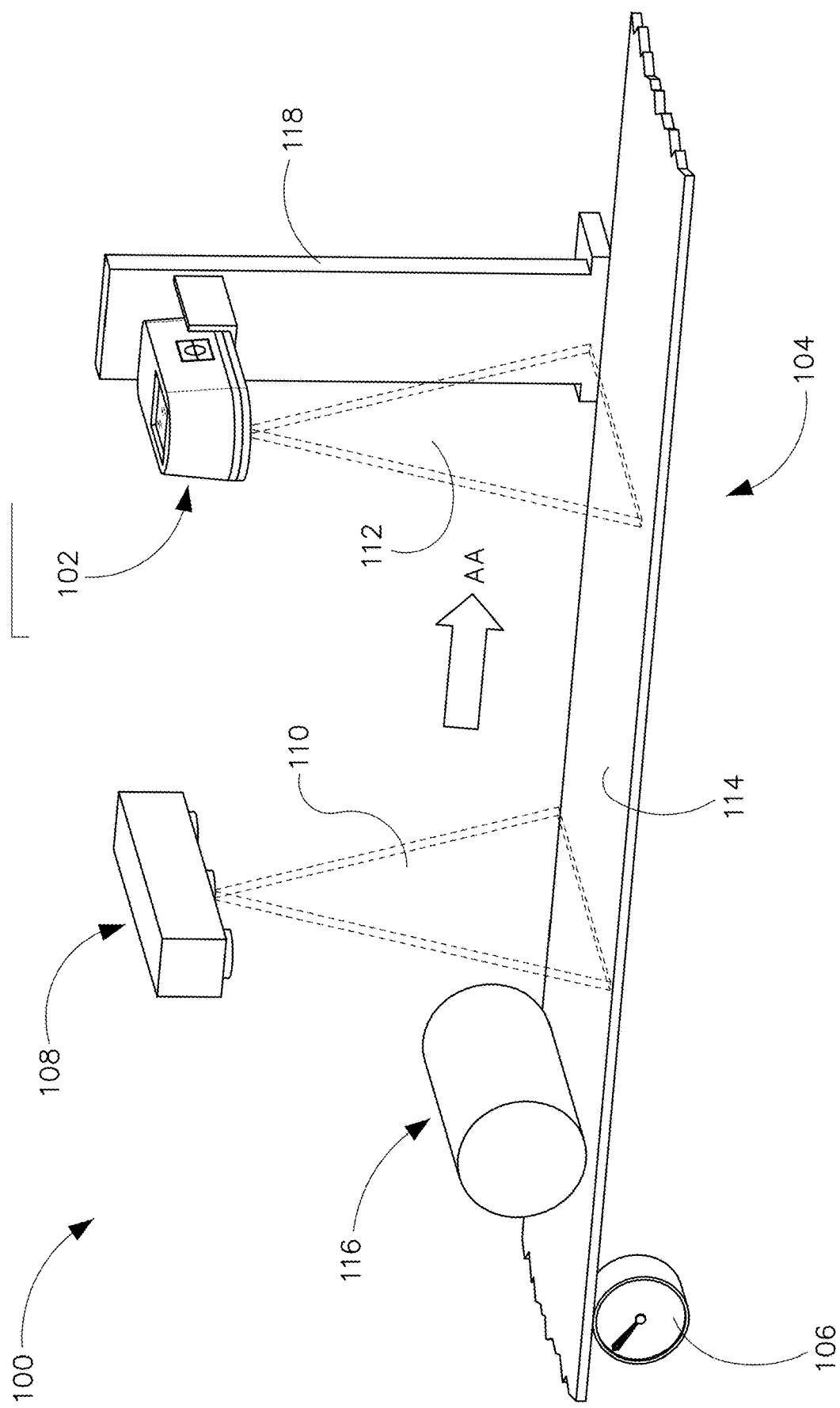
FIG. 2 is a perspective view of another embodiment of the coating status identification system.
Figure 6:
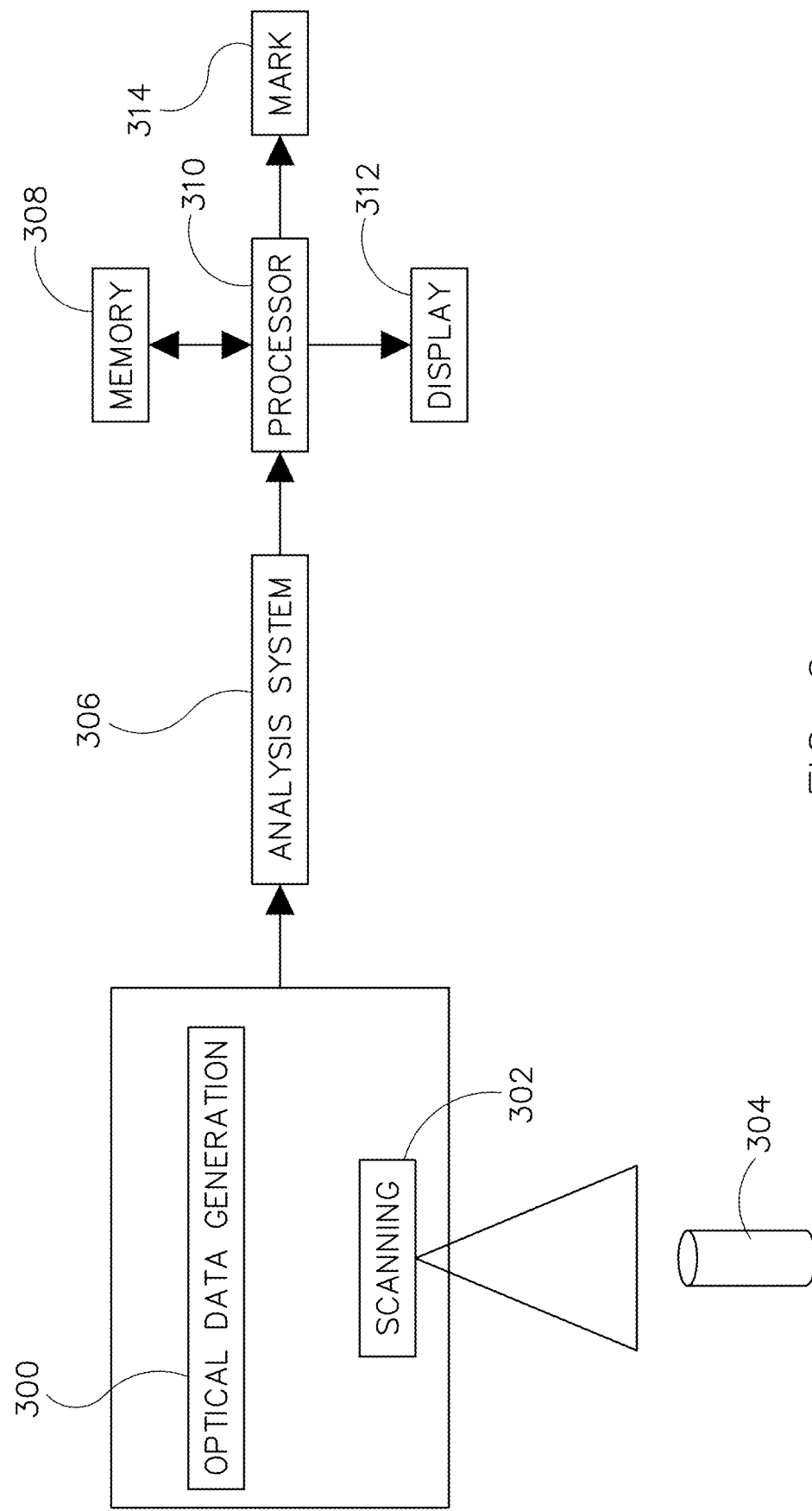
FIG. 6 is a block diagram of one embodiment of the coating status identification system, where the system will impart identification marking on bone material that has an acceptable coating disposed thereon (e.g., nanometer coating).

As illustrated in FIG. 1, in some embodiments, an identification system 100 is provided, the system comprising, consisting essentially of, or consisting of bone material 116 that needs an identification of a coating status (e.g., nanometer coating or nanometer structure), scanning device 102 configured to scan the bone material, the scanning device configured to transmit and/or receive data to and from a processor, the processor having logic to cause a computer to receive the scanned data, analyze the scanned data and display the coating status of the bone material based on the analyzed data when the coating status meets or fails to meet a predetermined parameter (e.g., a coating distribution on the bone material, coating thickness, coating nano structure, coating color, homogeneity, continuity, phase, composition or a combination thereof) as illustrated in FIG. 6. In some embodiments, the system is configured to scan bone material disposed on bed 114, where the bone material moves on conveyor belt 104. In some embodiments, the bone material is moving in a direction AA through a field of view 110 of a range finder 108. The range finder detects the presence of the bone material and determines the range, dimensions (e.g., height, width, length) and orientation of the object with respect to the conveyor belt. The respective range, dimensions, orientation and the coordination system of the conveyor belt and the scanning device are further illustrated in FIGS. 3 and 4. The range finder transmits dimensional data allowing the scanning device to use the information to focus its optics through a field of view of the scanning device 112 to maximize the efficiency and effectiveness of detecting and analyzing a coating status of the bone material. In some embodiments, the system also has a tachometer 106 measuring the speed and movement of the conveyor belt system to further control the geographical location of the bone material. In some embodiments, the system further includes an arm support 118, as illustrated in FIG. 2, connecting to the scanning device to facilitate the movement of the scanning device to further position the scanning device to scan the bone material. In some embodiments, the distance, the extent, and the orientation, including the angle of the scanning device or bone material, are controlled and adjusted by a user manually, such as with a handheld scanning device. In some embodiments, the scanning device is a handheld spectrophotometer. In some embodiments, the analysis involves comparing the scanned optical data to a predetermined parameter. The scanned option data and/or the predetermined parameter comprises light and absorption signals including spectral range over the ultra violet range from about 185 nm to about 400 nm; over the visible light range from about 400 nm to about 700 nm; and over the infrared range from about 700 nm to about 15000 nm. Some embodiments, the spectral range is from about 360 nm to about 780 nm. The optical data also comprises other parameters under the Beer-Lambert law including, but not limited to absorbance of light, light intensity, the optical path length, wavelength. The predetermined parameter comprises a coating distribution on the bone material, coating thickness, coating nanostructure, coating color or a combination thereof.

In some embodiments, the coated material to be identified is also applicable to an implant material, which include nature and synthetic material such as materials based on or include highly or fully demineralized bone, graphite or pyrolytic carbon, a mineral material such as hydroxyapatite, tricalcium phosphate, bioglass or other bioceramic or natural or synthetic polymers, e.g., bioabsorbable materials such as starches, polyglycolide, polylactide, glycolide-lactide copolymer, polyether ether ketone and the like, and nonbioabsorbable polymers such as polymethyl methacrylate, polytetrafluoroethylene, polyurethane, polyethylene and nylon.

In one embodiments, a sample of bone material (either the entire bone implant or a portion of the bone implant) can be disposed under the scanning device or inside a holding container or a holding surface inside the scanning device that is configured to allow scanning of the bone material, whether it is coated or uncoated. The sample for analysis of bone material can be in solid form (e.g., particles, shaped solid bone material, liquid form, semisolid form (e.g., paste, putty, gel etc.)) or a combination thereof.

In some embodiments, the sample of coated bone material can be used as a positive control or passing control, which is a bone sample that can have acceptable predetermined parameters including desirable coating distribution (e.g., uniform distribution), desired homogeneity, desired continuity, desirable coating thickness, desirable coating nano structure, desirable coating color, desired phase, desired composition, or a combination thereof. These parameters could be determined beforehand by SEM and this sample can be used as a positive control or passing control. This positive control can be scanned and analyzed using the system and methods of the current application and the data set for the positive control can be stored and used as a baseline data set to compare newly coated test samples that are scanned and analyzed, not with the SEM, but with the systems and methods of the current application. The new data set from the scanned and analyzed newly coated test samples can be compared to the data set baseline of the coated positive control and if they match or substantially match the display will indicate this to a user. If they do not match or substantially do not match the display will indicate a failed test and the coated test sample can be separated from the passing coated test samples. In this way a quantitative test can more efficiently and more cost effectively be done without the need to scan and analyze each test sample using the time consuming SEM steps.

In some embodiments, the sample of coated or uncoated bone material can be used as a negative control, which is a bone sample that can have unacceptable or failing predetermined parameters including undesirable coating distribution (e.g., non-uniform distribution), undesirable homogeneity, undesirable continuity, undesirable coating thickness, undesirable coating nano structure, undesirable coating color, undesirable phase, undesirable composition, or a combination thereof. These parameters could be determined beforehand by SEM and this sample can be used as a negative control having unacceptable or failing parameters. This negative control can be scanned and analyzed using the system and methods of the current application and the data set for the negative or failing control can be stored and used as a baseline data set to compare newly coated test samples that are scanned and analyzed, not with the SEM, but with the systems and methods of the current application. The new data set from the scanned and analyzed newly coated test samples can be compared to the data set baselines of the coated negative control and if they match or substantially match the display will indicate this to a user as a failed test and the coated test sample can be separated from the passing coated test samples. In this way a quantitative test can more efficiently and more cost effectively be done without the need to scan and analyze each test sample using the time consuming SEM steps.

The positive and negative controls can be used to calibrate the scanning device of the current application.

In some embodiments, the bone material is given a unique identifier associated with a blockchain structure. In some embodiments, the unique identifier is part of a blockchain system generated by a database that represents unique information, data or characteristics about the bone material.

Figure 3:
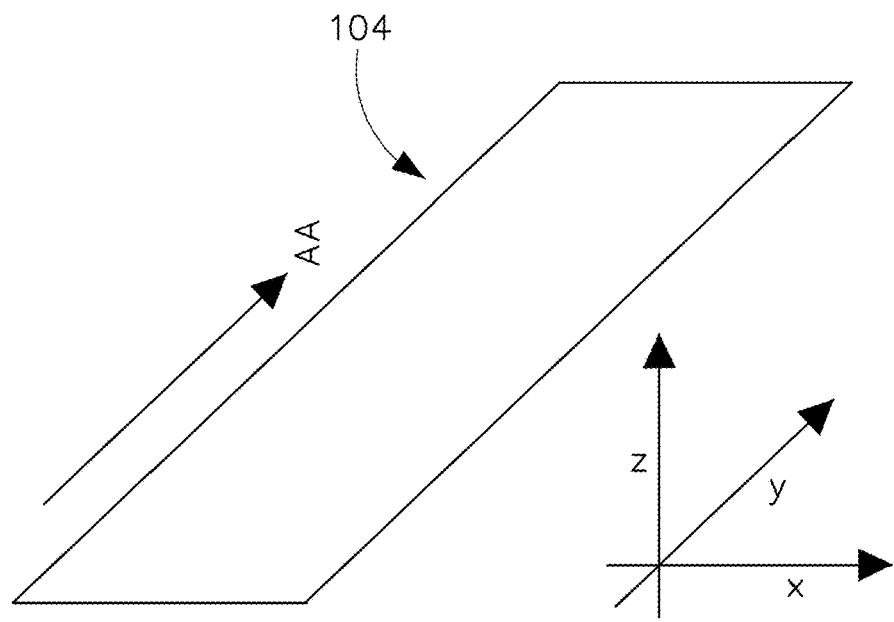
FIG. 3 is a conveyor belt coordinate system in accordance with one embodiment of the coating status identification system.
Figure 4:
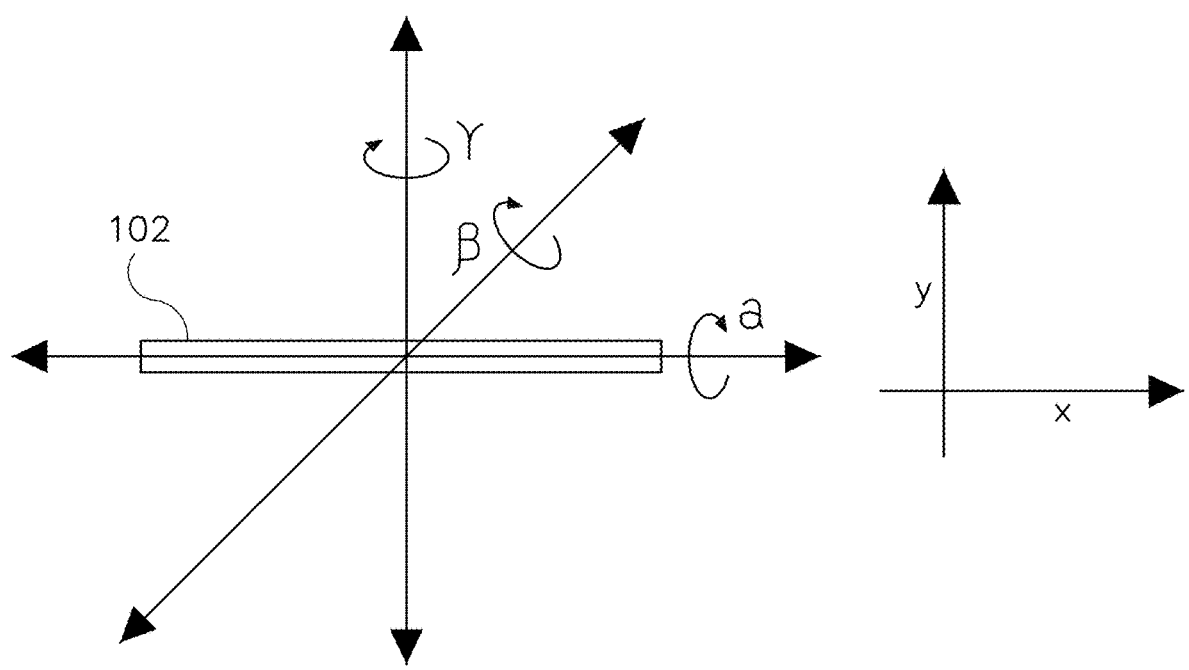
FIG. 4 is an instrument coordinate system in accordance with one embodiment of the coating status identification system.

In some embodiments, as illustrated in FIGS. 3 and 4, the range finder and/or the scanning device are setup for the bone material moving along y-axis in a direction AA while the range finder and/or the scanning device detects, senses or scans the bone material from above along z-axis, while the field of vision of the range finder and/or the scanning device extends across x-axis. In some embodiments, the range finder and/or the scanning device detects or scans the bone material at an angle. The angles of the range finder and/or the scanning device may be adjusted through their yaw angle, roll angle and pitch angle. In some embodiments, as the range finder and/or the scanning device will have a field of vision across the x-axis, the pitch angle $\alpha$ will rotate along the x-axis and the roll angle $\beta$ will rotate along the y-axis, and the yaw angle $\gamma$ will rotate along the z-axis.

Figure 5:
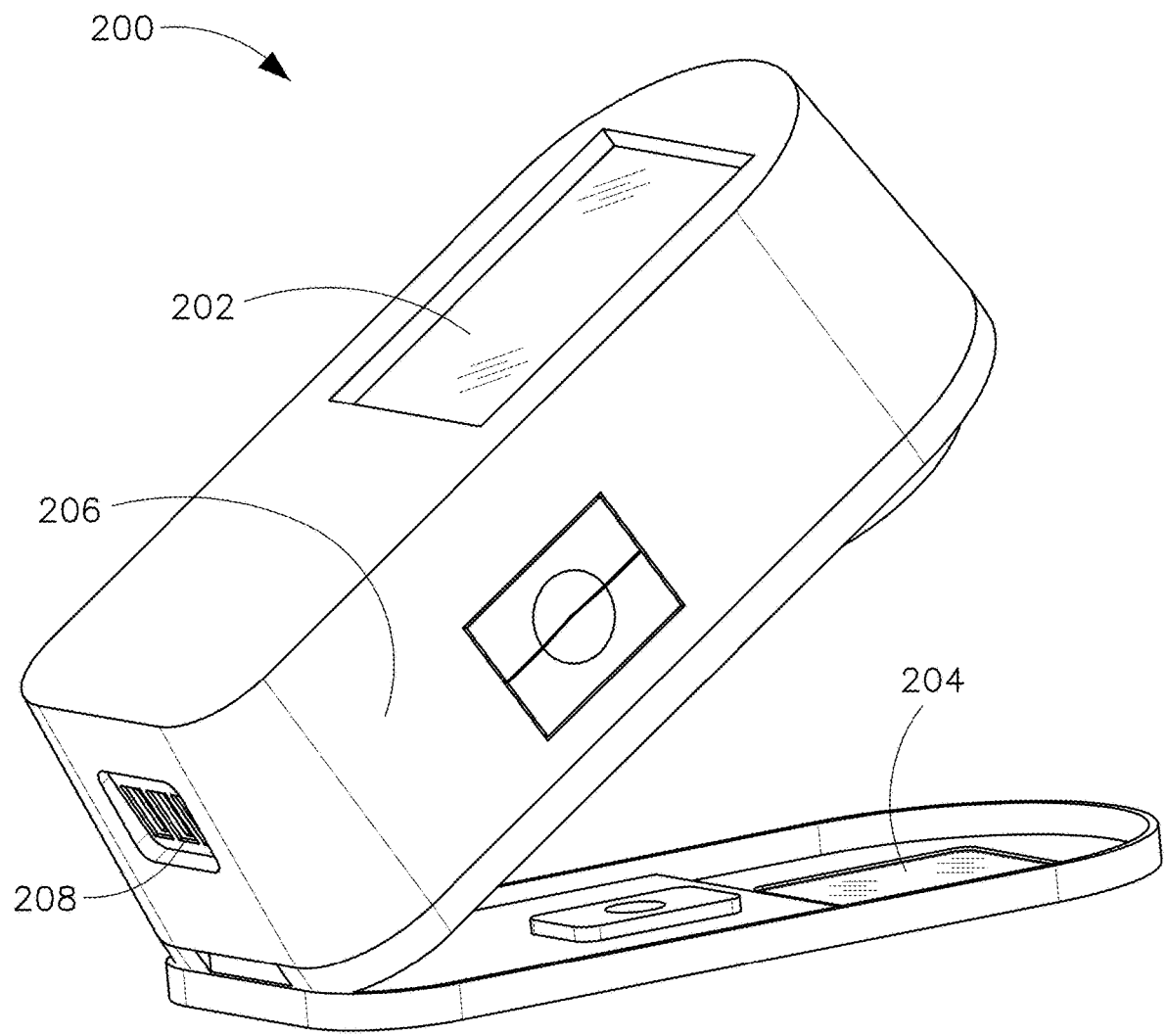
FIG. 5 is a perspective view of one embodiment of a hand-held spectrophotometer.

Illustrated in FIG. 5 is a handheld spectrophotometer 200, which comprises LED panel 202 configure to display a controlling menu and scanning parameter of the spectrophotometer. The spectrophotometer comprises an internal sensor 206 configured to measure the operating components inside the spectrophotometer for calibration. In some embodiments, the spectrophotometer comprises a preview window 204 allowing a user to verify and/or focus on the exact region in the bone material for identification and analysis. The spectrophotometer also comprises output ports 208 configured to transmit the scanned data to a processor or a computer, as described in other embodiments of the present application. In some embodiments, the scanning device is not limited to a handheld spectrophotometer. The scanning device comprises a lab instrument, a stationary instrument, or an inline setup that is configured to provide the optical data of the coating status of a material to be identified. It will be understood by those of ordinary skill in the art that the scanning device (e.g., spectrophotometer) can be an all-in-one single device and have the scanning device, the processor, and the display all as one single unit. Alternatively, one or more components of the scanning device can be separate components. For example, the scanning device can be a separate device from a processor that is in a computer that has a display.

FIG. 6 is a schematic block diagram of a system for scanning and identifying a coating status of bone material according to one embodiment of the present application. The system includes optical data generation 300 based on the images of bone material 304 captured by the scanning device 302. The optical data is sent to analysis system 306 to perform an analysis and comparison to a predetermined parameter. In some embodiments, a result or data from the identification is further sent to processor 310 for storage in a memory 308, which is then shown on a display 312. In some embodiments, the identification of the coating status is further marked 314 digitally on the bone material or recorded as an additional book to a blockchain structure associated with the bone material. In some embodiments, the bone material is marked physically on the bone material. This allows for easy tracking and identification of bone material should it be needed to, for example, identify the source of the bone material or recall the bone material or provide subsequent information about the bone material.

The processor can be part of a computer and comprises logic to execute one or more instructions from the reactor, for example, for the balance's rocking motions or the heating elements. The logic for executing instructions may be encoded in one or more tangible media for execution by the processor. For example, the processor may execute codes stored in a computer-readable medium such as memory 308. The computer-readable medium may be stored in, for example, electronic (for example, RAM (random access memory), ROM (read-only memory), EPROM (erasable programmable read-only memory), magnetic, optical (for example, CD (compact disc)), DVD (digital video disc), electromagnetic, semiconductor technology, or any other suitable medium. The computer includes logic to calculate the desired conditions for particular coating materials and bone materials. The execution of specific instructions are carried out by an input source to the coating system (for example, liquid input, gas input, thermo or temperature input and balance input, etc.).

The user can interface with the computer via a user interface that may include one or more display devices 312 (for example, CRT, LCD, touch screen, or other known displays) or other output devices (for example, printer, etc.), and one or more input devices (for example, keyboard, mouse, stylus, touch screen interface, or other known input mechanisms) for facilitating interaction of a user with the system via user interface. The user interface may be directly coupled to a database or directly coupled to a network server system via the Internet, Wi-Fi or cloud computing. In accordance with one embodiment, one or more user interfaces are provided as part of (or in conjunction with) the illustrated systems to permit users to interact with the systems.

The user interface device may be implemented as a graphical user interface (GUI) containing a display or the like, or may be a link to other user input/output devices known in the art. Individual ones of a plurality of devices (for example, network/stand-alone computers, personal digital assistants (PDAs), WebTV (or other Internet-only) terminals, set-top boxes, cellular phones, screen phones, pagers, blackberry, smart phones, iPhone, iPad, tablet, peer/non-peer technologies, kiosks, or other known (wired or wireless) communication devices, etc.) may similarly be used to execute one or more computer programs (for example, universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (for example, the Internet).

The database can be stored in storage devices or systems (for example, Random Access Memory (RAM), Read Only Memory (ROM), hard disk drive (MD), floppy drive, zip drive, compact disk-ROM, DVD, bubble memory, flash drive, redundant array of independent disks (RAID), network accessible storage (NAS) systems, storage area network (SAN) systems, e CAS (content addressed storage) or may also be one or more memory devices embedded within a CPU, or shared with one or more of the other components. The database may be deployed locally or remotely, relative to one or more components interacting with the memory or one or more modules. The database may include a data storage device, a collection component for collecting information from users or other computers into a centralized database, a tracking component for tracking information received and entered, a search component to search information in the database or other databases, a receiving component to receive a specific query from a user interface, and an accessing component to access centralized database. A receiving component is programmed for receiving a specific query from one of a plurality of users. The database may also include a processing component for searching and processing received queries against a data storage device containing a variety of information collected by a scanning device transferred to the processor, which includes wires, wireless and network connections as discussed below.

The disclosed system may, in some embodiments, be a computer network-based system. The computer network may take any wired/wireless form of known connective technology (for example, corporate or individual LAN, enterprise WAN, intranet, Internet, Virtual Private Network (VPN), combinations of network systems, etc.) to allow a server to provide local/remote information and control data to/from other locations (for example, other remote database servers, remote databases, network servers/user interfaces, etc.). In accordance with one embodiment, a network server may be serving one or more users over a collection of remote and disparate networks (for example, Internet, intranet, VPN, cable, special high-speed ISDN lines, etc.). The network may comprise one or more interfaces (for example, cards, adapters, ports) for receiving data, transmitting data to other network devices, and forwarding received data to internal components of the system. In accordance with one embodiment of the present application, the data may be downloaded in one or more textual/graphical formats (for example, RTF, PDF, TIFF, JPEG, STL, XML, XDFL, TXT etc.), or set for alternative delivery to one or more specified locations (for example, via e-mail, etc.) in any desired format (for example, print, storage on electronic media and/or computer readable storage media such as CD-ROM, etc.).

Figure 7:
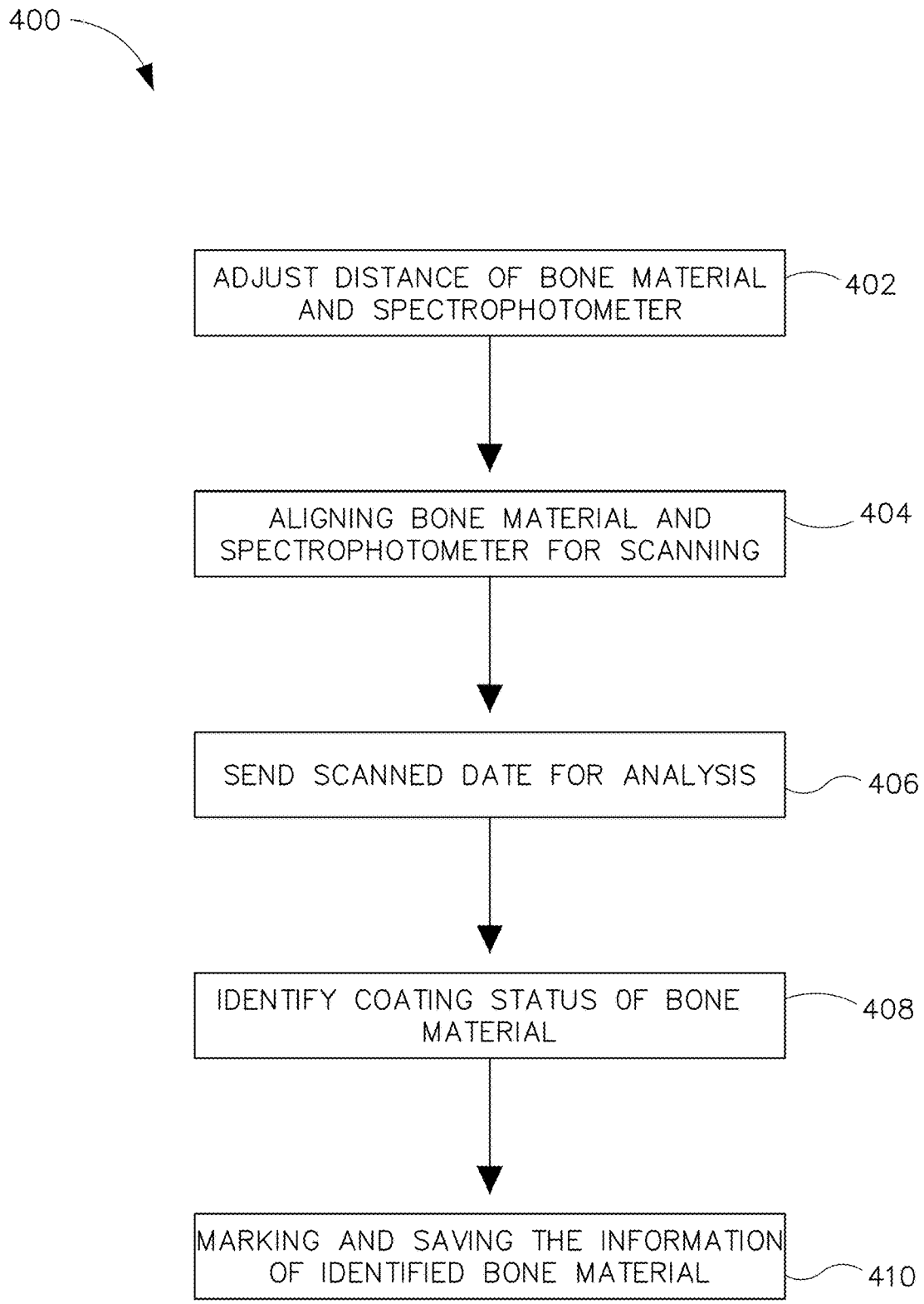
FIG. 7 is a flow chart of one embodiment of the methods used to identify a coating status of a bone material.

FIG. 7 is a flowchart of a method 400 for performing an identification of a coating status of a bone material. The bone material and the scanning device such as a spectrophotometer are prepared. The distance, orientation, angle, and other dimensional arrangements are adjusted 402. In some embodiments, the adjustment is completed through coordination among a conveyor belt, tachometer, range finder, arm support and/or other structures. In some embodiments, the adjustment is done manually by a user's hand. In some embodiments, a combination of machine and manual adjustments are used. After the adjustment, the bone material is moved to align with the scanning device for scanning 404. The scanning device can be aligned to any desirable region of the bone material. In some embodiments, the scanning is repeated multiple times to identify a specific spot of, a partial region of or the entire bone material. In some embodiments, the scanning device can align with the bone material to identify a specific region that is difficult to be identified by an electron microscope, or other digital microscope. After the scanning, the scanned data is sent to analyzer 406 for analysis. In some embodiments, the analyzer is a computer or a processor in accordance with one embodiment of the present application. After the analysis, the bone material is identified 408 based on the analysis. The identification information is further saved digitally to a database, a cloud server or a local computer; and/or the identification is marked physically onto the identified bone material 410.

Figure 8:
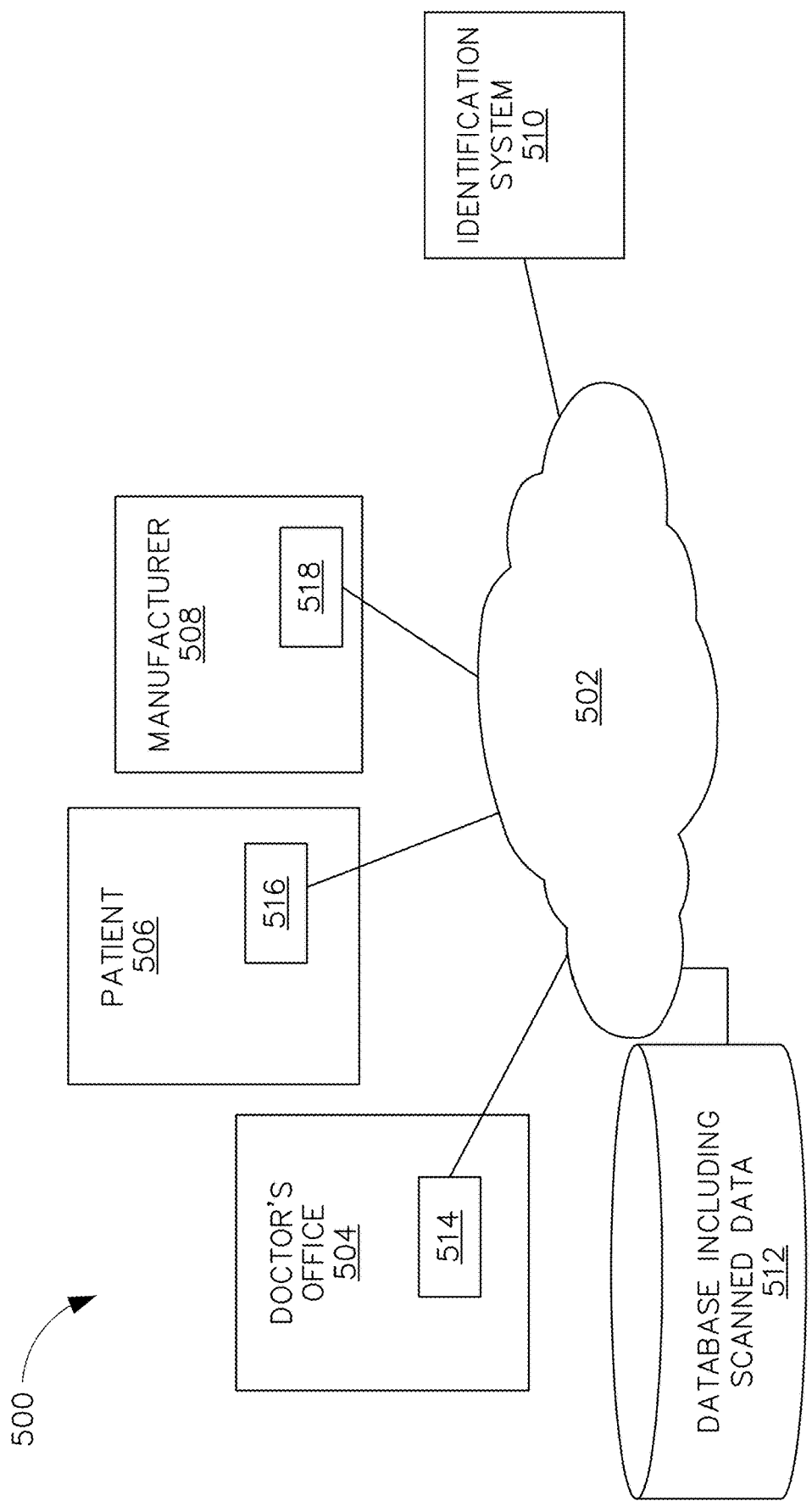
FIG. 8 is a diagram of a network in which embodiments of the current application may be practiced.

FIG. 8 is a diagram of an environment 500 in which embodiments may be practiced. The environment may include entities involved in processing information associated with the bone material, in accordance with some embodiments. Entities may include, but not be limited to, the doctor's office 504, patient 506, manufacturer 508, identification system 510 and the database 512, which included scanned data. The environment may include a computer device or processing unit that provides access to the database including a process unit from the doctor's office 514, a process unit from patient 516, a process unit from manufacturer 518, a network interface for communicating with each other and/or other electronic devices 502. The network may be a public switched telephone network (PSTN), a mobile communications network, a data network, such as a local area network (LAN) or wide area network (WAN), or a combination thereof, or other communication network known to those of ordinary skill in the art. In some embodiments, the information of a bone material including the coating status may be transmitted and authenticated through a peer-peer ledger system, which will prevent confusion and verification to ensure the use of coated or non-coated bone material.

A patient may visit the doctor's office, or a hospital, medical center, or other location where the patient may receive a bone material. The bone material information including the coating status may be supplied by the same medical entity. The manufacturer may access the network to receive information on the coating status for tracking or administrative purposes. In some embodiments, this information may be sent to a separate authentication processor ensure that the bone material has been verified.

Figure 9:
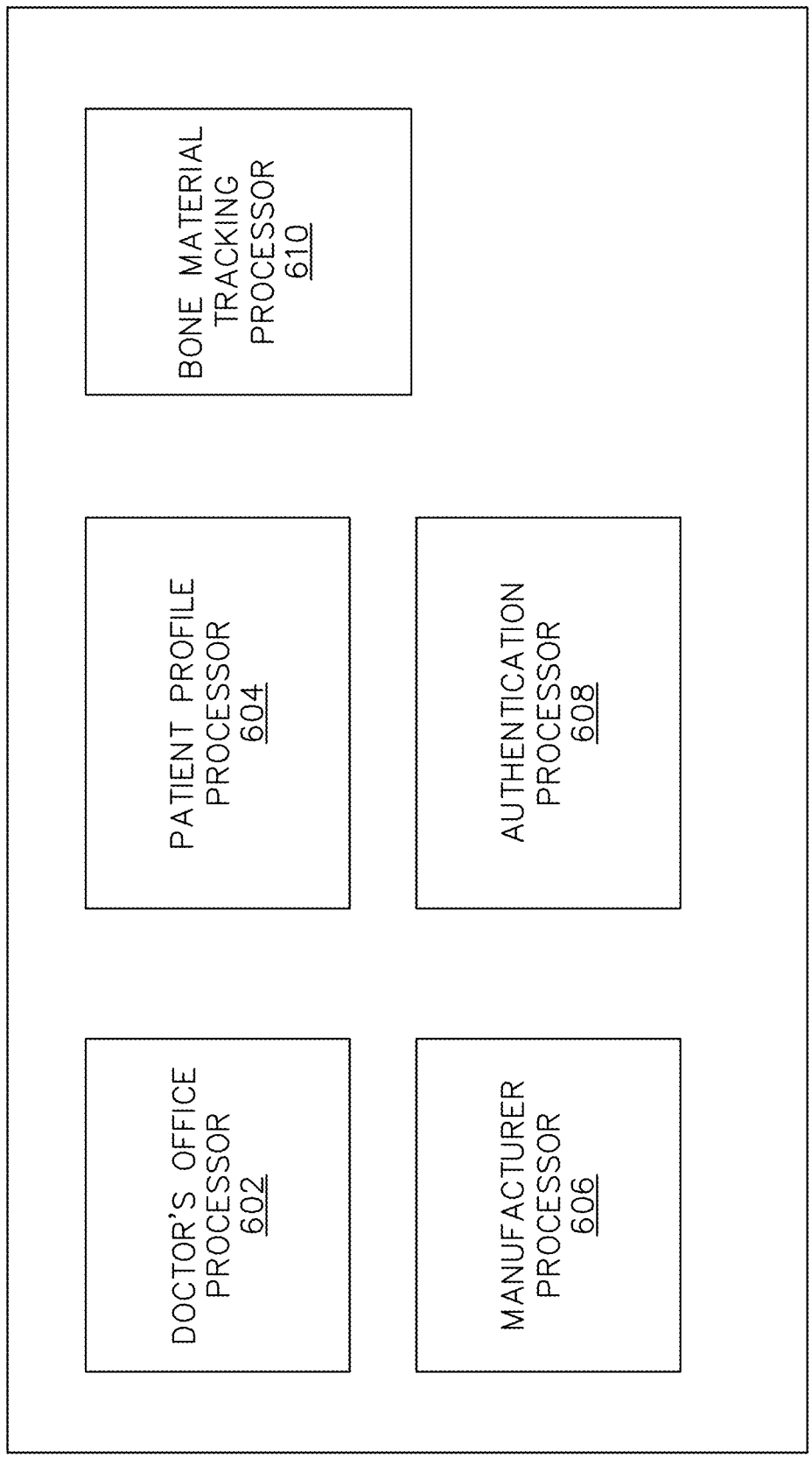
FIG. 9 is a block diagram of a processing system in accordance with some embodiments of the current application.

FIG. 9 is a block diagram of a processing system, in accordance with some embodiments of the present application. The processing system can be implemented in the environment illustrated and described with respect to FIG. 8. The identification processing system may include a doctor's office processor 602, a patient's medical profile processor 604, a pharmaceutical company or manufacturer processor 606, an authentication processor 608 and a bone material tracking processor 610. Some or all of these elements of the processing system may be present under a same computer hardware platform. In other embodiments, these elements may be located on two or more different computer hardware platforms and can communicate with each other and/or other elements of the processing system via the communication network, for example, a wired or wireless network that exchanges data electronically.

Figure 10:
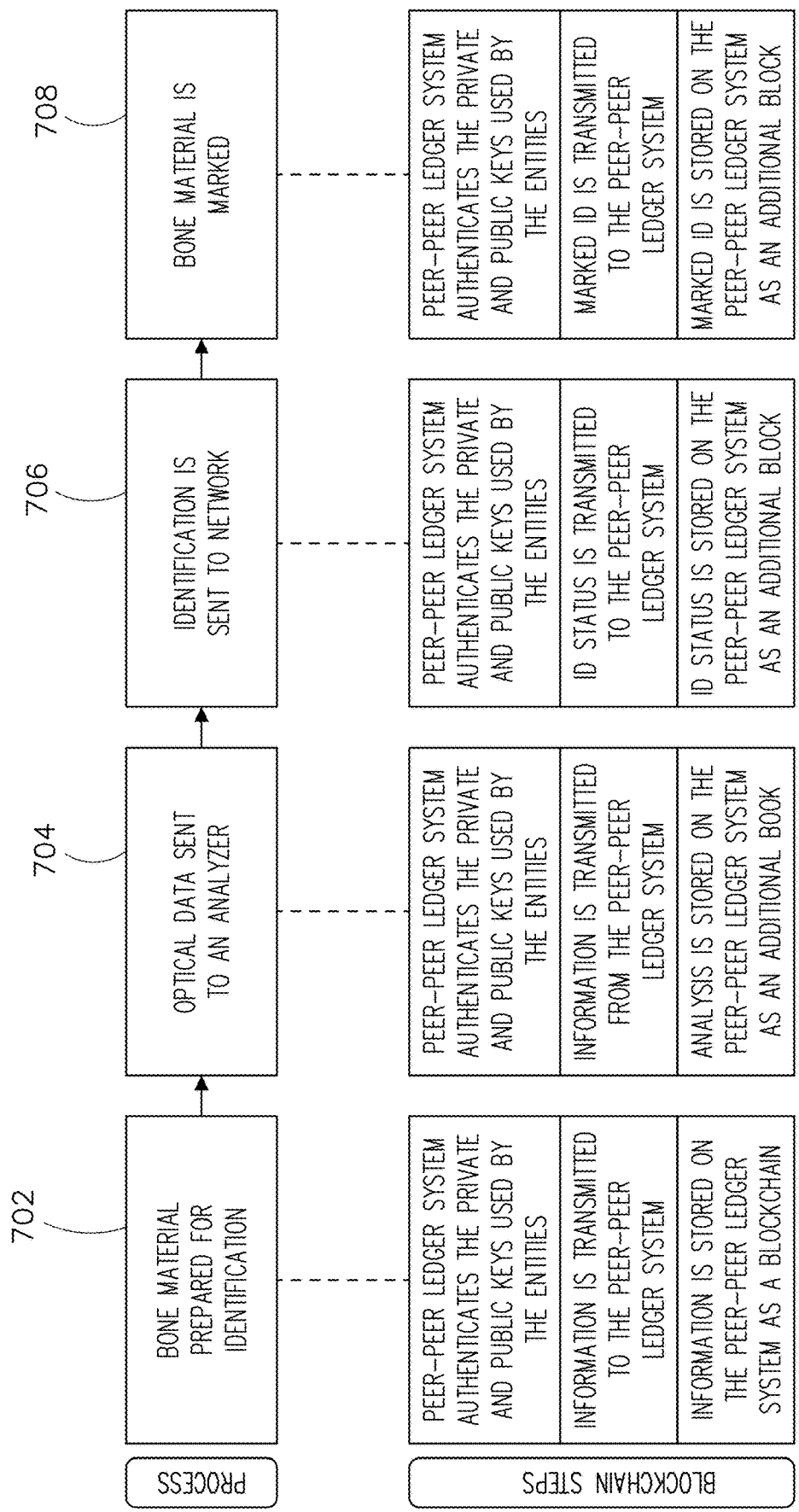
FIG. 10 is a process flow for the coating status of the bone material to be recorded and shared on a blockchain structure, in accordance with some embodiments of the current application.

FIG. 10 is a process flowchart 700 for the coating status identification of a bone material to be authenticated through a peer-peer ledger system, in accordance with some embodiments. In some embodiments, a process may include a method step of generating information associated with a bone material prepared for an identification process 702, a step of sending optical data to a processor, a computer, and/or an analyzer 704, a step of sending the identification result to a network for storage or further processing 706 and a step of marking the identification of the coating status digitally as an additional book onto a blockchain structure or marking the identification physically onto the bone material 708. Some or all of steps 702, 704, 706 and 708 may include a set of blockchain steps performed by a blockchain system including special purpose processors and memories, illustrated in FIG. 10. In some embodiments, marking is 3D printed, lasered, stamped, or a combination thereof on the bone material.

Figure 11:
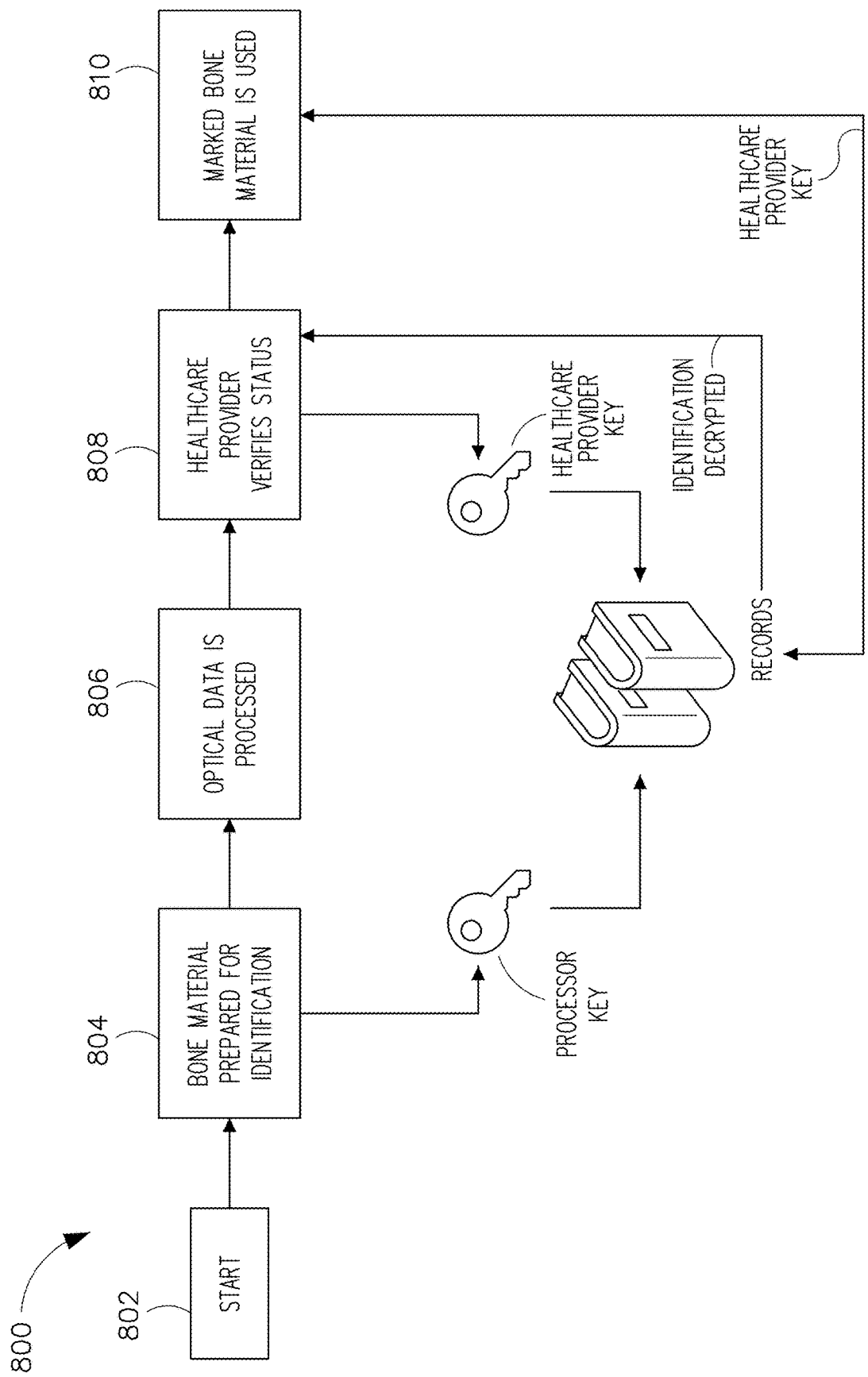
FIG. 11 is a process flow for generating, encrypting and sharing the information including the coating status of the bone material, in accordance with some embodiments of the current application.
Figure 12:
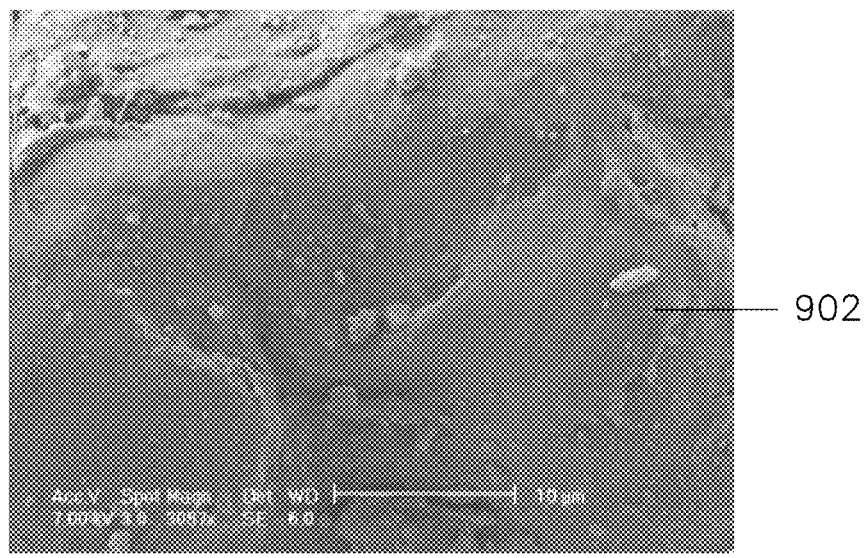
FIG. 12 is an SEM micrograph of an uncoated bone material.
Figure 13:
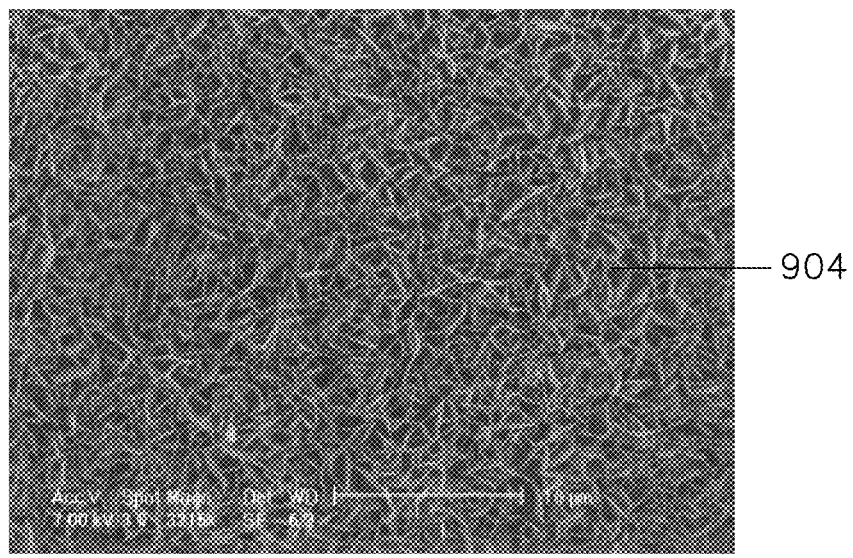
FIG. 13 is an SEM micrograph of a coated bone material.
Figure 14:
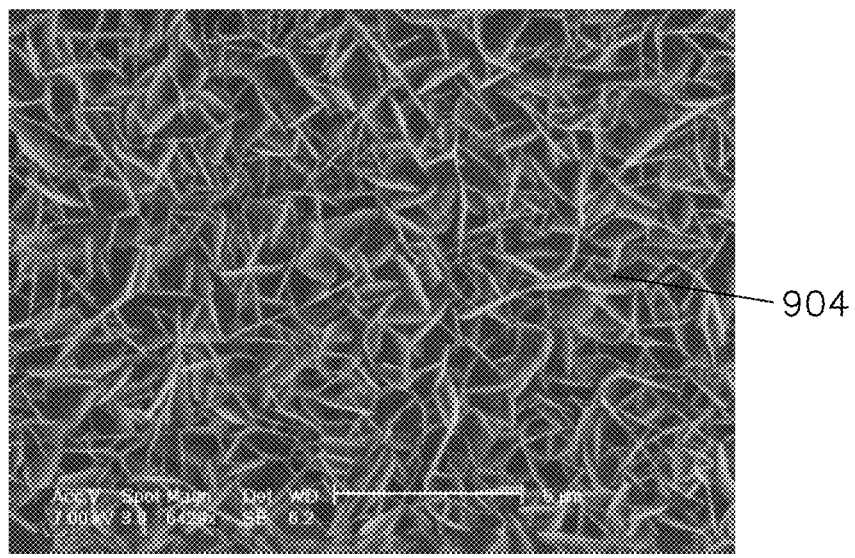
FIG. 14 is a higher magnification of an SEM micrograph as in FIG. 13.
Figure 15:
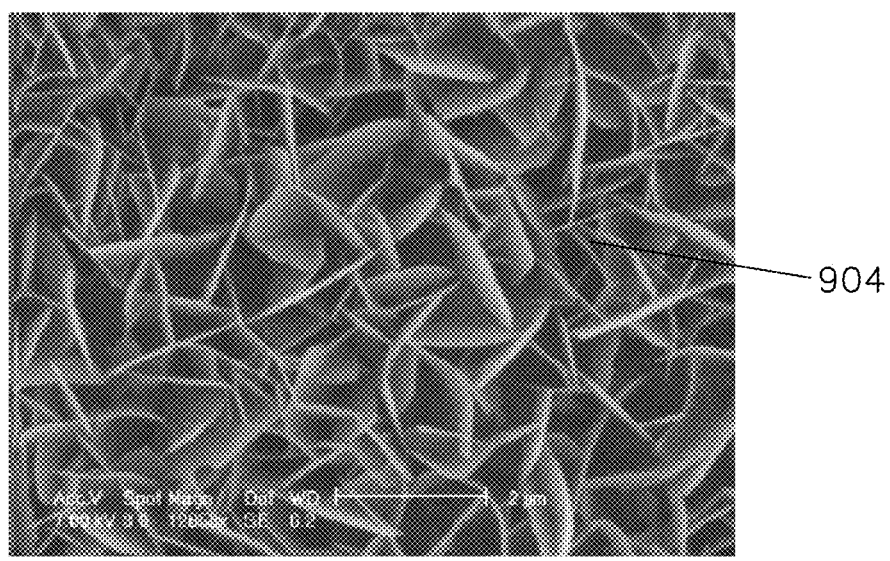
FIG. 15 is a higher magnification of an SEM micrograph as in FIG. 14.
Figure 16:
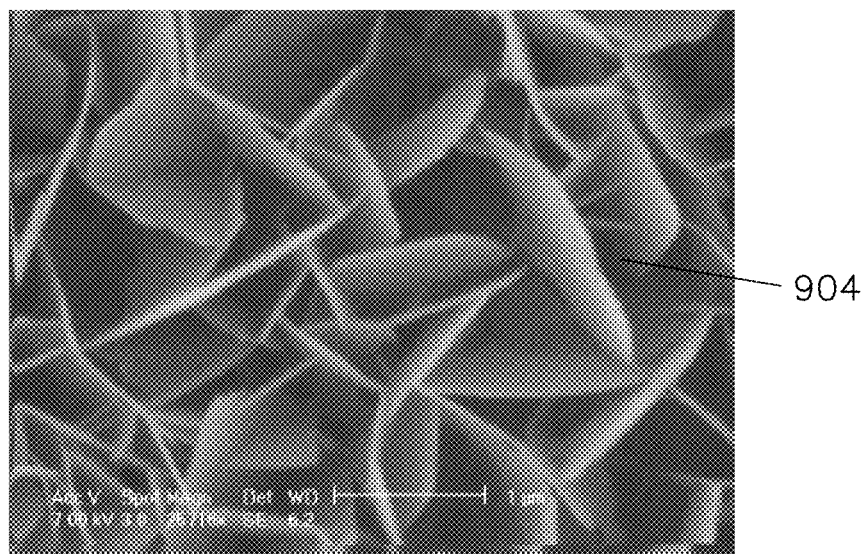
FIG. 16 is a higher magnification of an SEM micrograph as in FIG. 15.
Figure 17:
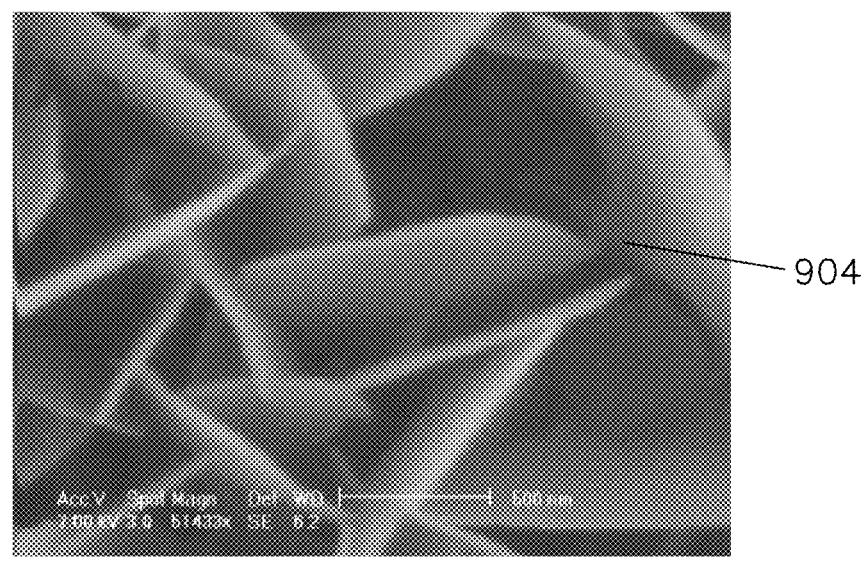
FIG. 17 is a higher magnification of an SEM micrograph as in FIG. 16.

FIG. 11 is a process flow for the coating status identification of a bone material to be shared through a peer-peer ledger system, in accordance with some embodiments. In some embodiments, a process 800 may include method steps of starting 802 by providing a system configured to scan a bone material for an identification process, associating the bone material with a blockchain structure 804 via a processor key, which encrypts the bone material information in records of a database, processing a scanned data 806 obtained from the system scanning the bone material, which can be stored or saved into record as an additional book, verifying the bone material information by a healthcare provider and/or a user 808 who needs to know the coating status of the bone material through a healthcare provider key, which decrypts the information including the identification of the coating status from the records of the database, and recording and/or saving the information to the records 810 via a healthcare provider key when the bone material is used. The process flow may include the use of a system comprising a blockchain for authentication. The blockchain may include an ongoing chain hashed with key addresses along the chain of custody, including hashing with a private key address, but not limited thereto. Here, a blockchain registers visit-related information, records, and/or other information exchanged in the process.

The blockchain system comprises one or more databases for the coating status associated with the bone material that includes entry data including, among other things, the bone materials' unique identifier, one or more parameters such as compositions of materials, identification dates, identified region, identification method, coating thickness, coating nanostructure, coating color or a combination thereof. This database can be searched by the user to ensure proper use and in this way the doctor can be assured that the proper coated or non-coated bone materials are used. In some embodiments, the blockchain system reduces misuse and guessing about the coating status of a bone material. Also, a particular bone material can then be tracked in the blockchain system to ensure that it is authentic is properly delivered, coated and verified to the manufacturer, distributor, and the patient. In some embodiments, the unique identifier is encrypted.

A blockchain system creates distributed documentation (outputs/transactions) in the form of a digital ledger available on a network of computers. When a transaction happens (e.g., a bone material is made or prepared for an identification), the users propose a record to the ledger. Records are bundled into blocks (groups for processing), and each block receives a unique fingerprint derived from the records it contains. Each block can include the fingerprint of the prior block, creating a robust chain of title. It is easy to verify the integrity of the entire chain, and nearly impossible to falsify historic records. In summary, a blockchain is a public ledger of transactions which critically provides trust based upon mathematics, rather than human relationships or institutions. A combination of public/private key cryptography and hash chains provides a mechanism to store arbitrary secure states as a single ledger—the blockchain—held at all distributed nodes. Nodes update their local state based on "proof of work" hashing algorithms applied to the system as a whole. These systems provide a secure mechanism for establishing shared common ground across many devices.

In some embodiments, a blockchain system may be a centralized reporting system that includes multiple sub-networks that communicate among patients, doctors, manufacturers, and/or pharmaceutical or medical device companies. At each transmission of communication, a new block may be formed with the subsequent blocks, which also includes handling, procurement, distribution, or acceptance of the bone material. The bone materials and their related compositions, products and their related inventory, retailer and their related inventory, and healthcare providers and their related inventory, will share their inventory statuses with the application or the blockchain structure, as blocks of information to a peer-to-peer ledger system, a sub-network among patients, doctors and manufacturer, or as inventory statuses with the application.

An entity such as the doctor or the doctor's office may provide an authentication or other security techniques including public and/or private keys when submitted associated with the bone material to be used in a surgery or an implant. Here, the consumer, a patient of the doctor, may also have a public and/or private key for communicating with the consumer's computer device and the doctor's office processor and/or other business entity computer device. When the bone material information is sent from the doctor's office processor or their affiliation to the manufacturer, it may include a converged blockchain structure of both the doctor's private/public key and the patient's private/public key. This information will be shared on a peer-to-peer network, where the manufacturer has access to the data, provided the manufacturer's key has been granted access to the bone material to be used. In some embodiments, the information is associated with a specific bone material for implant discussed above. More than a digital transaction among networks, the blockchain structure and the information can be incorporated into or onto a bone material via various imprinting methods (e.g., 3D printing, laser, stamp, etc.). In some embodiments, the information is a blockchain ID or other encrypted information inside the bone material or disposed on the bone material at one or more locations. In some embodiments, the blockchain ID or other encrypted information is disposed at discrete regions at or adjacent to the location where the bone material is disposed to ensure authentication of the bone material type. An inventory determination processor in coordination with the bone material tracking processor can monitor the use of the coated or non-coated bone material information.

FIGS. 12-17 illustrate the comparison of an uncoated bone material 902 and a coated bone material 904 in different magnification. The coated being mineralized coatings having a plate-like nanostructure of carbonate substituted, calcium-deficient hydroxyapatite (HA/TCP) shown in different magnifications in FIG. 13 (3,215×), FIG. 14 (6,429×), FIG. 15 (12,868×), FIG. 16 (25,716×) and FIG. 17 (51,433×). The resulting nanopore size varies from about 0.1 µm to about 0.2 µm. In these embodiments, the nanomorphology of the mineral coating increases the specific surface area of the bone implant and as a result it stimulates bone cell growth. In addition, the increased surface area further enhances early-stage dissolution increasing the availability of $Ca_2+$ and $PO_4-$, thus increasing new mineral deposition.

FIGS. 18-20 illustrate the comparison of an uncoated bone material and a coated material. FIG. 18 illustrates a cylindrical bone material comprising PEEK material 1000 in non-coated form 1002 and coated form 1004. FIG. 19 illustrates granule material 1100 in non-coated form 1102 and coated form 1104. FIG. 20 illustrates PCL strips 1200 in non-coated form 1202 and coated form 1204.

Bone Materials

The implant can comprise bone material. The bone material can be solid, semi-solid, or liquid form. The bone material can be in granular, paste, putty or powder forms. In some embodiments, the bone material can be demineralized bone material. The demineralized bone material can comprise demineralized bone, powder, chips, granules, shards, fibers or other shapes having irregular or random geometries. These can include, for example, substantially demineralized, partially demineralized, or fully demineralized cortical and cancellous bone. These also include surface demineralization, where the surface of the bone construct is substantially demineralized, partially demineralized, or fully demineralized, yet the body of the bone construct is fully mineralized. The configuration of the bone material can be obtained by milling, shaving, cutting or machining whole bone as described in, for example, U.S. Pat. No. 5,899,939. The entire disclosure is herein incorporated by reference into the present disclosure.

In some embodiments, the bone material can comprise elongated demineralized bone fibers having an average length to average thickness ratio or aspect ratio of the fibers from about 50:1 to about 1000:1. In overall appearance the elongated demineralized bone fibers can be round, spherical, granular, elongated, powders, chips, fibers, cylinders, threads, narrow strips, thin sheets, or a combination thereof. In some embodiments, the bone material comprises elongated demineralized bone fibers and chips. In some embodiments, the bone material comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the bone material comprises demineralized bone matrix fibers and demineralized bone matrix chips in a 30:60 ratio. In some embodiments, the bone material comprises demineralized bone matrix fibers and demineralized bone matrix chips in a ratio of 25:75 to about 75:25 fibers to chips.

In some embodiments, the bone material can be an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the bone material can comprise mineral particles, which comprise tricalcium phosphate and hydroxyapatite in a ratio of about 80:20 to about 90:10. In some embodiments, the mineral particles can comprise tricalcium phosphate and hydroxyapatite in a ratio of about 70:30 to about 95:5. In some embodiments, the mineral particles can comprise tricalcium phosphate and hydroxyapatite in a ratio of about 85:15.

In some embodiments, the bone material may be seeded with harvested bone cells and/or bone tissue, such as for example, cortical bone, autogenous bone, allogenic bones and/or xenogeneic bone while it is mixed.

In some embodiments, the bone material may be mixed with one or more therapeutic agents, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof. Recombinant BMP-2 can be used at a concentration of about 0.4 mg/mL to about 10.0 mg/mL, preferably about 1.5 mg/mL.

The bone material may include or be mixed with one or more members from the TGF-β superfamily. For example, the matrix may include AMH, ARTN, GDF1, GDF10, GDF11, GDF15, GDF2, GDF3, GDF3A, GDFS, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The bone material may include or be mixed with a therapeutic agent including, but not limited to, IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. The bone material may include or be mixed with therapeutic agents including excitatory amino acids such as glutamate and aspartate, antagonists or inhibitors of glutamate binding to NMDA receptors, AMPA receptors, and/or kainate receptors. The bone material may include or be mixed with therapeutic agents to reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

The bone material may include or be mixed with a therapeutic agent including, but not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The bone material may include or be mixed with a therapeutic agent including, but not limited to, an anti-inflammatory agent. An example of an anti-inflammatory agent includes, but is not limited to, clonidine, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The bone material may include or be mixed with a therapeutic agent including, but not limited to, a statin. Examples of a useful statin include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the bone material can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone;

nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; stefimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

The antimicrobial agent in the bone material can be an antiviral agent that can be mixed with the bone material. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

A bone material also includes the porous ceramic granules that are like the granules found and described in U.S. application Ser. No. 16/523,259, filed on Jul. 26, 2019, assigned to Warsaw Orthopedic, Inc., which is incorporated herein by reference in its entirety. The porous ceramic granules have an average diameter from about 50 μm to 1.6 mm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 850, 900, 950, 1000, 1100, 1150, 1200, 1250, 1300, 1350, 1400, 1450, 1500, 1550 to about 1600 μm. It is to be understood that the ceramic material is smaller in size than the macroparticles.

When the porous ceramic granules are used in the composition, the granules are in an amount from about 50 to about 98 wt. % and the collagen is in an amount from about 2 to about 50 wt. % based on a total weight of each of the lyophilized porous macroparticles. Each of the porous ceramic granules comprise hydroxyapatite and beta-tricalcium phosphate having a calcium to phosphate ratio of between 1.0 to about 2.0, as described above regarding the ceramic material.

Each of the porous ceramic granules have a Brunauer-Emmett-Teller (BET) surface area from about 0.2 to about 10 m2/g. The BET surface area can be from about 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 m2/g. The increase in surface area further facilitates new bone growth by allowing the granules to dissolve and release calcium faster than a granule would.

Each of the porous ceramic granules can have a microporosity, and the diameter of the micropores is from about 0.01 to about 10 microns. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 microns. In some embodiments, the median pore diameter can be about 125 μm and the average pore diameter can be 78 μm.

In some embodiments, the ceramic material is a combination of a calcium phosphate ceramic and a silicon ceramic. In some embodiments, the calcium phosphate ceramic is resorbable biphasic calcium phosphate (BCP) or resorbable tri-calcium phosphate (TCP).

The ceramic material of the disclosure may also be oxide ceramics such as alumina (Al2O3) or zirconia (ZrO2) or composite combinations of oxides and non-oxides such as silicon nitride.

In various embodiments, the bone material comprise ceramic material in an amount from about 50 to about 98 wt. % and collagen in an amount from about 2 to about 50 wt. % based on a total weight of the bone material. In other embodiments the bone material described in this application is rollable and has a thickness of from about 1 mm to about 4 mm and comprises up to 83% ceramic material. In some embodiments, the bone material has a surface area of at least about 5 m2/g, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 m2/g.

Mineral Coating

The implant can comprise bone material and have a mineral coating. The bone material, including a scaffold, or portion or component thereof, described herein can include a surface modification or a coating. The mineral coating of a scaffold, as described herein, can be performed by any conventional manner. A mineral coating can be as described in U.S. application Ser. Nos. 13/407,441; 13/879,178; and 13/036,470 and are incorporated by reference.

In some embodiments, there are exemplary methods for producing coated scaffolds (e.g., bone material) using a mineral coating solution. For example, the mineral coating solution can be a modified simulated body fluid (mSBF). By adjusting the mineral composition, and/or concentration of the mSBF, the composition of the mineral precipitated on the scaffolds can be manipulated. See also U.S. Patent Publication No. US 2008/0095817 A1; U.S. Pat. No. 6,767,928 B1, U.S. Pat. No. 6,541,022 B1, PCT Publication WO 2008/070355 A2; PCT Publication WO 2008/082766 A2; Murphy and Mooney, 2001; and Murphy and Messersmith, 2000.

As described herein, the mineral coating can be calcium-containing. For example, the calcium-containing mineral coating can include hydroxyapatite (HAP), α-tricalcium phosphate (α-TCP), β-tricalcium phosphate (β-TCP), amorphous calcium phosphate, dicalcium phosphate, octacalcium phosphate, calcium phosphate (CaP), or calcium carbonate. The calcium-containing mineral coating can comprise a plurality of layers, e.g., separate layers having distinct dissolution profiles. Under physiological conditions, solubility of calcium phosphate species can adhere to the following trend: amorphous calcium phosphate>dicalcium phosphate>octacalcium phosphate>β-TCP>HAP. A dicalcium phosphate mineral can have a dissolution rate that is more than fifty times higher than that of HAP. Therefore, creation of a matrix with distinct calcium phosphate layers allows for a broad range of dissolution patterns.

For example, a mineral coating can be according to ISO 2337 'Implants for surgery—In vitro evaluation for apatite-forming ability of implant materials.' As another example, a mineral coating can be an adapted protocol according to ISO 2337 'Implants for surgery—In vitro evaluation for apatite-forming ability of implant materials.' As another example, the mineral coating can be performed by immersing a scaffold into a modified simulated body fluid at physiological conditions and continuous rotations. Continuous rotations can replenish the modified simulated body fluid, replace the modified simulated body fluid, or remove and add modified simulated body fluid.

As described herein, the scaffold can be incubated in modified simulated body fluid (mSBF) solutions to induce formation of a calcium phosphate-based mineral layer for mineral nucleation and growth. The mSBF solution can contain ionic constituents of blood plasma, with double the concentrations of calcium and phosphate ions, held at physiologic temperature and pH. The growth of calcium phosphate-based minerals, specifically bone-like minerals, on bioresorbable polymer matrices using mSBF incubation has been demonstrated (Lin et al., 2004; Murphy et al., 2002, 2005).

As described herein, a mineral coating of a scaffold, as described herein, can be performed by incubating a scaffold. For example, the mineral coating, described herein, can be developed by incubating the constituents in modified simulated body fluid (mSBF), for five days or less (e.g., 3-4 days) at a pH of about 6.8 to about 7.4 and at a temperature of about 25° C.-37° C. The SBF or mSBF can be refreshed daily. Using the chemical composition, the procedure produces a calcium-deficient, carbonate-containing apatite material on alginate and on poly-(α-hydroxy esters). See U.S. Pat. No. 6,767,928, incorporated herein by reference. mSBF can include elevated calcium and phosphate. In general, an increase in pH can favor hydroxyapatite growth, while a decrease in pH can favor octacalcium phosphate mineral growth.

As another example, conditions favorable for hydroxyapatite formation can include a pH between about 5.0 and about 8.0 and a calcium concentration multiplied by a phosphate concentration between about 10-5 M and about 10-8 M. Likewise, conditions favorable for octacalcium phosphate formation include a pH between about 6.0 and about 8.0 and a calcium concentration multiplied by a phosphate concentration between about 10-5 M and about 10-7.5 M. Furthermore, conditions favorable for dicalcium phosphate dehydrate formation can include a pH between about 6.0 and about 8.0 and a calcium concentration multiplied by a phosphate concentration between about 10-4 M and about 10-6 M.

As another example, one could vary the pH of mSBF between about 5.0 and about 6.0 to promote hydroxyapatite formation. Similarly, one could vary the pH of mSBF between about 6.0 and about 6.5 to promote octacalcium phosphate and hydroxyapatite formation. Likewise, one could vary the pH of mSBF between about 6.5 and about 8.0 to promote dicalcium phosphate, octacalcium phosphate, and hydroxyapatite formation.

As another example, the scaffold can be incubated for at least about 1 day; at least about 2 days; at least about 3 days; at least about 4 days; at least about 5 days; at least about 6 days; at least about 7 days; at least about 8 days; at least about 9 days; at least about 10 days; at least about 11 days; at least about 12 days; at least about 13 days; at least about 14 days; at least about 15 days; at least about 16 days; at least about 17 days; at least about 18 days; at least about 19 days; at least about 20 days; at least about 21 days; at least about 22 days; at least about 23 days; at least about 24 days; at least about 25 days; at least about 26 days; at least about 27 days; at least about 28 days; at least about 29 days; or at least about 30 days. It is understood that recitation of the above discrete values includes a range between each recited value.

For example, the scaffold can be incubated for about 1 day; about 2 days; about 3 days; about 4 days; about 5 days; about 6 days; about 7 days; about 8 days; about 9 days; about 10 days; about 11 days; about 12 days; about 13 days; about 14 days; about 15 days; about 16 days; about 17 days; about 18 days; about 19 days; about 20 days; about 21 days; about 22 days; about 23 days; about 24 days; about 25 days; about 26 days; about 27 days; about 28 days; about 29 days; or about 30 days. It is understood that recitation of the above discrete values includes a range between each recited value.

A mineral coating of a scaffold, as described herein, can be performed by incubating a scaffold at a temperature. For example, the scaffold can be incubated at a physiologically relevant temperature. As another example, the scaffold can be incubated at a temperature of about 1° C.; about 2° C.; about 3° C.; about 4° C.; about 5° C.; about 6° C.; about 7° C.; about 8° C.; about 9° C.; about 10° C.; about 11° C.; about 12° C.; about 13° C.; about 14° C.; about 15° C.; about 16° C.; about 17° C.; about 18° C., about 19° C., about 20° C., about 21° C.; about 22° C.; about 23° C.; about 24° C.; about 25° C.; about 26° C.; about 27° C.; about 28° C.; about 29° C.; about 30° C.; about 31° C.; about 32° C.; about 33° C.; about 34° C.; about 35° C.; about 36° C.; about 37° C.; about 38° C.; about 39° C.; about 40° C.; about 41° C.; about 42° C.; about 43° C.; about 44° C.; about 45° C.; about 46° C.; about 47° C.; about 48° C.; about 49° C.; about 50° C.; about 51° C.; about 52° C.; about 53° C.; about 54° C.; about 55° C.; about 56° C.; about 57° C.; about 58° C.; about 59° C.; about 60° C.; about 61° C.; about 62° C.; about 63° C.; about 64° C.; about 65° C.; about 66° C.; about 67° C.; about 68° C.; about 69° C.; about 70° C.; about 71° C.; about 72° C.; about 73° C.; about 74° C.; about 75° C.; about 76° C.; about 77° C.; about 78° C.; about 79° C.; about 80° C.; about 81° C.; about 82° C.; about 83° C.; about 84° C.; about 85° C.; about 86° C.; about 87° C.; about 88° C.; about 89° C.; about 90° C.; about 91° C.; about 92° C.; about 93° C.; about 94° C.; about 95° C.; about 96° C.; about 97° C.; about 98° C.; about 99° C.; or about 100° C. It is understood that recitation of the above discrete values includes a range between each recited value.

A scaffold, or portion or component thereof, can be coated individually or in groups using, for example, a CaP coating technology. A scaffold, or portion or component thereof, can be modified individually or in groups using a technique such as aminolysis for RGD attachment, chemical conjugation, layer by layer deposition, or chemical vapor deposition.

Prior to deposition of the first calcium-containing mineral, the scaffold may be surface-functionalized to allow increased mineral deposition by utilizing chemical pre-treatment to achieve surface hydrolysis (e.g., using an NaOH solution). Surface degradation by this technique can cause an increase in the amount of polar oxygen functional groups on the surface of the material.

The functionalized surface can then be incubated in a mineral-containing solution (e.g., modified simulated body fluid). The mineral coating process, as described herein, can mimic natural biomineralization processes.

The mineral coating, as described herein, can be similar in structure and composition to human bone mineral. For example, the mineral coating can include spherical clusters with a plate-like structure or a plate-like structure and a carbonate-substituted, calcium deficient hydroxyapatite phase composition. As another example, the coating can be an osteoconductive mineral coating.

As another example, the mineral coating can include an apatite. Apatite can include calcium phosphate, calcium carbonate, calcium fluoride, calcium hydroxide, or citrate.

As another example, a mineral coating can comprise a plurality of discrete mineral islands on the scaffold, or the mineral coating can be formed on the entire surface of the scaffold. As another example, the mineral coating can comprise a substantially homogeneous mineral coating. In other embodiments, the mineral coatings can be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, or a mixture thereof. For example, an osteoconductive mineral coating can be calcium-deficient carbonate-containing hydroxyapatite.

As another example, the mineral coating can include hydroxyapatite. Calcium deficient hydroxyapatite can have a formula of $Ca_{10-x}(PO_4)_{6-x}(HPO_4)_x(OH)_{2-x}$. Stoichiometric hydroxyapatite can have a chemical formula of $Ca_{10}(PO_4)_6(OH)_2$ or can be also written as $Ca_5(PO_4)_3(OH)$. Hydroxyapatite can be predominantly crystalline but may be present in amorphous forms.

The mineral coating, as described herein, can include at least about 1% hydroxyapatite. For example, the mineral coating can include at least about 1% hydroxyapatite; at least about 2% hydroxyapatite; at least about 3% hydroxyapatite; at least about 4% hydroxyapatite; at least about 5% hydroxyapatite; at least about 6% hydroxyapatite; at least about 7% hydroxyapatite; at least about 8% hydroxyapatite; at least about 9% hydroxyapatite; at least about 10% hydroxyapatite; at least about 11% hydroxyapatite; at least about 12% hydroxyapatite; at least about 13% hydroxyapatite; at least about 14% hydroxyapatite; at least about 15% hydroxyapatite; at least about 16% hydroxyapatite; at least about 17% hydroxyapatite; at least about 18% hydroxyapatite; at least about 19% hydroxyapatite; at least about 20% hydroxyapatite; at least about 21% hydroxyapatite; at least about 22% hydroxyapatite; at least about 23% hydroxyapatite; at least about 24% hydroxyapatite; at least about 25% hydroxyapatite; at least about 26% hydroxyapatite; at least about 27% hydroxyapatite; at least about 28% hydroxyapatite; at least about 29% hydroxyapatite; at least about 30% hydroxyapatite; at least about 31% hydroxyapatite; at least about 32% hydroxyapatite; at least about 33% hydroxyapatite; at least about 34% hydroxyapatite; at least about 35% hydroxyapatite; at least about 36% hydroxyapatite; at least about 37% hydroxyapatite; at least about 38% hydroxyapatite; at least about 39% hydroxyapatite; at least about 40% hydroxyapatite; at least about 41% hydroxyapatite; at least about 42% hydroxyapatite; at least about 43% hydroxyapatite; at least about 44% hydroxyapatite; at least about 45% hydroxyapatite; at least about 46% hydroxyapatite; at least about 47% hydroxyapatite; at least about 48% hydroxyapatite; at least about 49% hydroxyapatite; at least about 50% hydroxyapatite; at least about 51% hydroxyapatite; at least about 52% hydroxyapatite; at least about 53% hydroxyapatite; at least about 54% hydroxyapatite; at least about 55% hydroxyapatite; at least about 56% hydroxyapatite; at least about 57% hydroxyapatite; at least about 58% hydroxyapatite; at least about 59% hydroxyapatite; at least about 60% hydroxyapatite; at least about 61% hydroxyapatite; at least about 62% hydroxyapatite; at least about 63% hydroxyapatite; at least about 64% hydroxyapatite; at least about 65% hydroxyapatite; at least about 66% hydroxyapatite; at least about 67% hydroxyapatite; at least about 68% hydroxyapatite; at least about 69% hydroxyapatite; at least about 70% hydroxyapatite; at least about 71% hydroxyapatite; at least about 72% hydroxyapatite; at least about 73% hydroxyapatite; at least about 74% hydroxyapatite; at least about 75% hydroxyapatite; at least about 76% hydroxyapatite; at least about 77% hydroxyapatite; at least about 78% hydroxyapatite; at least about 79% hydroxyapatite; at least about 80% hydroxyapatite; at least about 81% hydroxyapatite; at least about 82% hydroxyapatite; at least about 83% hydroxyapatite; at least about 84% hydroxyapatite; at least about 85% hydroxyapatite; at least about 86% hydroxyapatite; at least about 87% hydroxyapatite; at least about 88% hydroxyapatite; at least about 89% hydroxyapatite; at least about 90% hydroxyapatite; at least about 91% hydroxyapatite; at least about 92% hydroxyapatite; at least about 93% hydroxyapatite; at least about 94% hydroxyapatite; at least about 95% hydroxyapatite; at least about 96% hydroxyapatite; at least about 97% hydroxyapatite; at least about 98% hydroxyapatite; at least about 99% hydroxyapatite; or at least about 100% hydroxyapatite. It is understood that recitation of the above discrete values includes a range between each recited value.

As another example, the mineral coating can include about 1% hydroxyapatite; about 2% hydroxyapatite; about 3% hydroxyapatite; about 4% hydroxyapatite; about 5% hydroxyapatite; about 6% hydroxyapatite; about 7% hydroxyapatite; about 8% hydroxyapatite; about 9% hydroxyapatite; about 10% hydroxyapatite; about 11% hydroxyapatite; about 12% hydroxyapatite; about 13% hydroxyapatite; about 14% hydroxyapatite; about 15% hydroxyapatite; about 16% hydroxyapatite; about 17% hydroxyapatite; about 18% hydroxyapatite; about 19% hydroxyapatite; about 20% hydroxyapatite; about 21% hydroxyapatite; about 22% hydroxyapatite; about 23% hydroxyapatite; about 24% hydroxyapatite; about 25% hydroxyapatite; about 26% hydroxyapatite; about 27% hydroxyapatite; about 28% hydroxyapatite; about 29% hydroxyapatite; about 30% hydroxyapatite; about 31% hydroxyapatite; about 32% hydroxyapatite; about 33% hydroxyapatite; about 34% hydroxyapatite; about 35% hydroxyapatite; about 36% hydroxyapatite; about 37% hydroxyapatite; about 38% hydroxyapatite; about 39% hydroxyapatite; about 40% hydroxyapatite; about 41% hydroxyapatite; about 42% hydroxyapatite; about 43% hydroxyapatite; about 44% hydroxyapatite; about 45% hydroxyapatite; about 46% hydroxyapatite; about 47% hydroxyapatite; about 48% hydroxyapatite; about 49% hydroxyapatite; about 50% hydroxyapatite; about 51% hydroxyapatite; about 52% hydroxyapatite; about 53% hydroxyapatite; about 54% hydroxyapatite; about 55% hydroxyapatite; about 56% hydroxyapatite; about 57% hydroxyapatite; about 58% hydroxyapatite; about 59% hydroxyapatite; about 60% hydroxyapatite; about 61% hydroxyapatite; about 62% hydroxyapatite; about 63% hydroxyapatite; about 64% hydroxyapatite; about 65% hydroxyapatite; about 66% hydroxyapatite; about 67% hydroxyapatite; about 68% hydroxyapatite; about 69% hydroxyapatite; about 70% hydroxyapatite; about 71% hydroxyapatite; about 72% hydroxyapatite; about 73% hydroxyapatite; about 74% hydroxyapatite; about 75% hydroxyapatite; about 76% hydroxyapatite; about 77% hydroxyapatite; about 78% hydroxyapatite; about 79% hydroxyapatite; about 80% hydroxyapatite; about 81% hydroxyapatite; about 82% hydroxyapatite; about 83% hydroxyapatite; about 84% hydroxyapatite; about 85% hydroxyapatite; about 86% hydroxyapatite; about 87% hydroxyapatite; about 88% hydroxyapatite; about 89% hydroxyapatite; about 90% hydroxyapatite; about 91% hydroxyapatite; about 92% hydroxyapatite; about 93% hydroxyapatite; about 94% hydroxyapatite; about 95% hydroxyapatite; about 96% hydroxyapatite; about 97% hydroxyapatite; about 98% hydroxyapatite; about 99% hydroxyapatite; or about 100% hydroxyapatite. It is understood that recitation of the above discrete values includes a range between each recited value.

The mineral coating, as described herein, can include octacalcium phosphate. Octacalcium phosphate has a chemical formula of $Ca_8H_2(PO_4)_6 \cdot 5H_2O$ or can also be written as $Ca_4HO_{12}P_3$. Octacalcium phosphate has been shown to be a precursor of hydroxyapatite. Hydrolysis of Octacalcium phosphate can create hydroxyapatite. Octacalcium phosphate can be predominantly crystalline but may be present in amorphous forms.

The mineral coating, as described herein, can include at least about 1% octacalcium phosphate. For example, the mineral coating can include at least about 1% octacalcium phosphate; at least about 2% octacalcium phosphate; at least about 3% octacalcium phosphate; at least about 4% octacalcium phosphate; at least about 5% octacalcium phosphate; at least about 6% octacalcium phosphate; at least about 7% octacalcium phosphate; at least about 8% octacalcium phosphate; at least about 9% octacalcium phosphate; at least about 10% octacalcium phosphate; at least about 11% octacalcium phosphate; at least about 12% octacalcium phosphate; at least about 13% octacalcium phosphate; at least about 14% octacalcium phosphate; at least about 15% octacalcium phosphate; at least about 16% octacalcium phosphate; at least about 17% octacalcium phosphate; at least about 18% octacalcium phosphate; at least about 19% octacalcium phosphate; at least about 20% octacalcium phosphate; at least about 21% octacalcium phosphate; at least about 22% octacalcium phosphate; at least about 23% octacalcium phosphate; at least about 24% octacalcium phosphate; at least about 25% octacalcium phosphate; at least about 26% octacalcium phosphate; at least about 27% octacalcium phosphate; at least about 28% octacalcium phosphate; at least about 29% octacalcium phosphate; at least about 30% octacalcium phosphate; at least about 31% octacalcium phosphate; at least about 32% octacalcium phosphate; at least about 33% octacalcium phosphate; at least about 34% octacalcium phosphate; at least about 35% octacalcium phosphate; at least about 36% octacalcium phosphate; at least about 37% octacalcium phosphate; at least about 38% octacalcium phosphate; at least about 39% octacalcium phosphate; at least about 40% octacalcium phosphate; at least about 41% octacalcium phosphate; at least about 42% octacalcium phosphate; at least about 43% octacalcium phosphate; at least about 44% octacalcium phosphate; at least about 45% octacalcium phosphate; at least about 46% octacalcium phosphate; at least about 47% octacalcium phosphate; at least about 48% octacalcium phosphate; at least about 49% octacalcium phosphate; at least about 50% octacalcium phosphate; at least about 51% octacalcium phosphate; at least about 52% octacalcium phosphate; at least about 53% octacalcium phosphate; at least about 54% octacalcium phosphate; at least about 55% octacalcium phosphate; at least about 56% octacalcium phosphate; at least about 57% octacalcium phosphate; at least about 58% octacalcium phosphate; at least about 59% octacalcium phosphate; at least about 60% octacalcium phosphate; at least about 61% octacalcium phosphate; at least about 62% octacalcium phosphate; at least about 63% octacalcium phosphate; at least about 64% octacalcium phosphate; at least about 65% octacalcium phosphate; at least about 66% octacalcium phosphate; at least about 67% octacalcium phosphate; at least about 68% octacalcium phosphate; at least about 69% octacalcium phosphate; at least about 70% octacalcium phosphate; at least about 71% octacalcium phosphate; at least about 72% octacalcium phosphate; at least about 73% octacalcium phosphate; at least about 74% octacalcium phosphate; at least about 75% octacalcium phosphate; at least about 76% octacalcium phosphate; at least about 77% octacalcium phosphate; at least about 78% octacalcium phosphate; at least about 79% octacalcium phosphate; at least about 80% octacalcium phosphate; at least about 81% octacalcium phosphate; at least about 82% octacalcium phosphate; at least about 83% octacalcium phosphate; at least about 84% octacalcium phosphate; at least about 85% octacalcium phosphate; at least about 86% octacalcium phosphate; at least about 87% octacalcium phosphate; at least about 88% octacalcium phosphate; at least about 89% octacalcium phosphate; at least about 90% octacalcium phosphate; at least about 91% octacalcium phosphate; at least about 92% octacalcium phosphate; at least about 93% octacalcium phosphate; at least about 94% octacalcium phosphate; at least about 95% octacalcium phosphate; at least about 96% octacalcium phosphate; at least about 97% octacalcium phosphate; at least about 98% octacalcium phosphate; at least about 99% octacalcium phosphate; or at least about 100% octacalcium phosphate. It is understood that recitation of the above discrete values includes a range between each recited value.

As another example, the mineral coating can include about 1% octacalcium phosphate; about 2% octacalcium phosphate; about 3% octacalcium phosphate; about 4% octacalcium phosphate; about 5% octacalcium phosphate; about 6% octacalcium phosphate; about 7% octacalcium phosphate; about 8% octacalcium phosphate; about 9% octacalcium phosphate; about 10% octacalcium phosphate; about 11% octacalcium phosphate; about 12% octacalcium phosphate; about 13% octacalcium phosphate; about 14% octacalcium phosphate; about 15% octacalcium phosphate; about 16% octacalcium phosphate; about 17% octacalcium phosphate; about 18% octacalcium phosphate; about 19% octacalcium phosphate; about 20% octacalcium phosphate; about 21% octacalcium phosphate; about 22% octacalcium phosphate; about 23% octacalcium phosphate; about 24% octacalcium phosphate; about 25% octacalcium phosphate; about 26% octacalcium phosphate; about 27% octacalcium phosphate; about 28% octacalcium phosphate; about 29% octacalcium phosphate; about 30% octacalcium phosphate; about 31% octacalcium phosphate; about 32% octacalcium phosphate; about 33% octacalcium phosphate; about 34% octacalcium phosphate; about 35% octacalcium phosphate; about 36% octacalcium phosphate; about 37% octacalcium phosphate; about 38% octacalcium phosphate; about 39% octacalcium phosphate; about 40% octacalcium phosphate; about 41% octacalcium phosphate; about 42% octacalcium phosphate; about 43% octacalcium phosphate; about 44% octacalcium phosphate; about 45% octacalcium phosphate; about 46% octacalcium phosphate; about 47% octacalcium phosphate; about 48% octacalcium phosphate; about 49% octacalcium phosphate; about 50% octacalcium phosphate; about 51% octacalcium phosphate; about 52% octacalcium phosphate; about 53% octacalcium phosphate; about 54% octacalcium phosphate; about 55% octacalcium phosphate; about 56% octacalcium phosphate; about 57% octacalcium phosphate; about 58% octacalcium phosphate; about 59% octacalcium phosphate; about 60% octacalcium phosphate; about 61% octacalcium phosphate; about 62% octacalcium phosphate; about 63% octacalcium phosphate; about 64% octacalcium phosphate; about 65% octacalcium phosphate; about 66% octacalcium phosphate; about 67% octacalcium phosphate; about 68% octacalcium phosphate; about 69% octacalcium phosphate; about 70% octacalcium phosphate; about 71% octacalcium phosphate; about 72% octacalcium phosphate; about 73% octacalcium phosphate; about 74% octacalcium phosphate; about 75% octacalcium phosphate; about 76% octacalcium phosphate; about 77% octacalcium phosphate; about 78% octacalcium phosphate; about 79% octacalcium phosphate; about 80% octacalcium phosphate; about 81% octacalcium phosphate; about 82% octacalcium phosphate; about 83% octacalcium phosphate; about 84% octacalcium phosphate; about 85% octacalcium phosphate; about 86% octacalcium phosphate; about 87% octacalcium phosphate; about 88% octacalcium phosphate; about 89% octacalcium phosphate; about 90% octacalcium phosphate; about 91% octacalcium phosphate; about 92% octacalcium phosphate; about 93% octacalcium phosphate; about 94% octacalcium phosphate; about 95% octacalcium phosphate; about 96% octacalcium phosphate; about 97% octacalcium phosphate; about 98% octacalcium phosphate; about 99% octacalcium phosphate; or about 100% octacalcium phosphate. It is understood that recitation of the above discrete values includes a range between each recited value.

The mineral coating, as described herein, can include at least about 1% porosity. For example, the mineral coating, as described herein, can include a porosity of at least about 1% porosity; at least about 2% porosity; at least about 3% porosity; at least about 4% porosity; at least about 5% porosity; at least about 6% porosity; at least about 7% porosity; at least about 8% porosity; at least about 9% porosity; at least about 10% porosity; at least about 11% porosity; at least about 12% porosity; at least about 13% porosity; at least about 14% porosity; at least about 15% porosity; at least about 16% porosity; at least about 17% porosity; at least about 18% porosity; at least about 19% porosity; at least about 20% porosity; at least about 21% porosity; at least about 22% porosity; at least about 23% porosity; at least about 24% porosity; at least about 25% porosity; at least about 26% porosity; at least about 27% porosity; at least about 28% porosity; at least about 29% porosity; at least about 30% porosity; at least about 31% porosity; at least about 32% porosity; at least about 33% porosity; at least about 34% porosity; at least about 35% porosity; at least about 36% porosity; at least about 37% porosity; at least about 38% porosity; at least about 39% porosity; at least about 40% porosity; at least about 41% porosity; at least about 42% porosity; at least about 43% porosity; at least about 44% porosity; at least about 45% porosity; at least about 46% porosity; at least about 47% porosity; at least about 48% porosity; at least about 49% porosity; at least about 50% porosity; at least about 51% porosity; at least about 52% porosity; at least about 53% porosity; at least about 54% porosity; at least about 55% porosity; at least about 56% porosity; at least about 57% porosity; at least about 58% porosity; at least about 59% porosity; at least about 60% porosity; at least about 61% porosity; at least about 62% porosity; at least about 63% porosity; at least about 64% porosity; at least about 65% porosity; at least about 66% porosity; at least about 67% porosity; at least about 68% porosity; at least about 69% porosity; at least about 70% porosity; at least about 71% porosity; at least about 72% porosity; at least about 73% porosity; at least about 74% porosity; at least about 75% porosity; at least about 76% porosity; at least about 77% porosity; at least about 78% porosity; at least about 79% porosity; at least about 80% porosity; at least about 81% porosity; at least about 82% porosity; at least about 83% porosity; at least about 84% porosity; at least about 85% porosity; at least about 86% porosity; at least about 87% porosity; at least about 88% porosity; at least about 89% porosity; at least about 90% porosity; at least about 91% porosity; at least about 92% porosity; at least about 93% porosity; at least about 94% porosity; at least about 95% porosity; at least about 96% porosity; at least about 97% porosity; at least about 98% porosity; at least about 99% porosity; or at least about 100% porosity. It is understood that recitation of the above discrete values includes a range between each recited value.

As another example, the mineral coating can include about 1% porosity; about 2% porosity; about 3% porosity; about 4% porosity; about 5% porosity; about 6% porosity; about 7% porosity; about 8% porosity; about 9% porosity; about 10% porosity; about 11% porosity; about 12% porosity; about 13% porosity; about 14% porosity; about 15% porosity; about 16% porosity; about 17% porosity; about 18% porosity; about 19% porosity; about 20% porosity; about 21% porosity; about 22% porosity; about 23% porosity; about 24% porosity; about 25% porosity; about 26% porosity; about 27% porosity; about 28% porosity; about 29% porosity; about 30% porosity; about 31% porosity;

about 32% porosity; about 33% porosity; about 34% porosity; about 35% porosity; about 36% porosity; about 37% porosity; about 38% porosity; about 39% porosity; about 40% porosity; about 41% porosity; about 42% porosity; about 43% porosity; about 44% porosity; about 45% porosity; about 46% porosity; about 47% porosity; about 48% porosity; about 49% porosity; about 50% porosity; about 51% porosity; about 52% porosity; about 53% porosity; about 54% porosity; about 55% porosity; about 56% porosity; about 57% porosity; about 58% porosity; about 59% porosity; about 60% porosity; about 61% porosity; about 62% porosity; about 63% porosity; about 64% porosity; about 65% porosity; about 66% porosity; about 67% porosity; about 68% porosity; about 69% porosity; about 70% porosity; about 71% porosity; about 72% porosity; about 73% porosity; about 74% porosity; about 75% porosity; about 76% porosity; about 77% porosity; about 78% porosity; about 79% porosity; about 80% porosity; about 81% porosity; about 82% porosity; about 83% porosity; about 84% porosity; about 85% porosity; about 86% porosity; about 87% porosity; about 88% porosity; about 89% porosity; about 90% porosity; about 91% porosity; about 92% porosity; about 93% porosity; about 94% porosity; about 95% porosity; about 96% porosity; about 97% porosity; about 98% porosity; about 99% porosity; or about 100% porosity. It is understood that recitation of the above discrete values includes a range between each recited value.

The mineral coating, as described herein, can include a pore diameter between about 1 nm and about 3500 nm. As another example, the mineral coating, as described herein, can include a pore diameter between about 100 and about 350 nm. As another example, the mineral coating, as described herein, can include at least about 1 nm pore diameter; at least about 10 nm pore diameter; at least about 15 nm pore diameter; at least about 20 nm pore diameter; at least about 25 nm pore diameter; at least about 30 nm pore diameter; at least about 35 nm pore diameter; at least about 40 nm pore diameter; at least about 45 nm pore diameter; at least about 50 nm pore diameter; at least about 55 nm pore diameter; at least about 60 nm pore diameter; at least about 65 nm pore diameter; at least about 70 nm pore diameter; at least about 75 nm pore diameter; at least about 80 nm pore diameter; at least about 85 nm pore diameter; at least about 90 nm pore diameter; at least about 95 nm pore diameter; at least about 100 nm pore diameter; at least about 105 nm pore diameter; at least about 110 nm pore diameter; at least about 115 nm pore diameter; at least about 120 nm pore diameter; at least about 125 nm pore diameter; at least about 130 nm pore diameter; at least about 135 nm pore diameter; at least about 140 nm pore diameter; at least about 145 nm pore diameter; at least about 150 nm pore diameter; at least about 155 nm pore diameter; at least about 160 nm pore diameter; at least about 165 nm pore diameter; at least about 170 nm pore diameter; at least about 175 nm pore diameter; at least about 180 nm pore diameter; at least about 185 nm pore diameter; at least about 190 nm pore diameter; at least about 195 nm pore diameter; at least about 200 nm pore diameter; at least about 205 nm pore diameter; at least about 210 nm pore diameter; at least about 215 nm pore diameter; at least about 220 nm pore diameter; at least about 225 nm pore diameter; at least about 230 nm pore diameter; at least about 235 nm pore diameter; at least about 240 nm pore diameter; at least about 245 nm pore diameter; at least about 250 nm pore diameter; at least about 255 nm pore diameter; at least about 260 nm pore diameter; at least about 265 nm pore diameter; at least about 270 nm pore diameter; at least about 275 nm pore diameter; at least about 280 nm pore diameter; at least about 285 nm pore diameter; at least about 290 nm pore diameter; at least about 295 nm pore diameter; at least about 300 nm pore diameter; at least about 305 nm pore diameter; at least about 310 nm pore diameter; at least about 315 nm pore diameter; at least about 320 nm pore diameter; at least about 325 nm pore diameter; at least about 330 nm pore diameter; at least about 335 nm pore diameter; at least about 340 nm pore diameter; at least about 345 nm pore diameter; at least about 350 nm pore diameter; at least about 355 nm pore diameter; at least about 360 nm pore diameter; at least about 365 nm pore diameter; at least about 370 nm pore diameter; at least about 375 nm pore diameter; at least about 400 nm pore diameter; at least about 410 nm pore diameter; at least about 420 nm pore diameter; at least about 430 nm pore diameter; at least about 440 nm pore diameter; at least about 450 nm pore diameter; at least about 460 nm pore diameter; at least about 470 nm pore diameter; at least about 480 nm pore diameter; at least about 490 nm pore diameter; at least about 500 nm pore diameter; at least about 600 nm pore diameter; at least about 700 nm pore diameter; at least about 800 nm pore diameter; at least about 900 nm pore diameter; at least about 1000 nm pore diameter; at least about 1100 nm pore diameter; at least about 1200 nm pore diameter; at least about 1300 nm pore diameter; at least about 1400 nm pore diameter; at least about 1500 nm pore diameter; at least about 1600 nm pore diameter; at least about 1700 nm pore diameter; at least about 1800 nm pore diameter; at least about 1900 nm pore diameter; at least about 2000 nm pore diameter; at least about 2100 nm pore diameter; at least about 2200 nm pore diameter; at least about 2300 nm pore diameter; at least about 2400 nm pore diameter; at least about 2500 nm pore diameter; at least about 2600 nm pore diameter; at least about 2700 nm pore diameter; at least about 2800 nm pore diameter; at least about 2900 nm pore diameter; at least about 3000 nm pore diameter; at least about 3100 nm pore diameter; at least about 3200 nm pore diameter; at least about 3300 nm pore diameter; at least about 3400 nm pore diameter; or at least about 3500 nm pore diameter. It is understood that recitation of the above discrete values includes a range between each recited value.

As another example, the mineral coating, as described herein, can include about 1 nm pore diameter; about 10 nm pore diameter; about 20 nm pore diameter; about 30 nm pore diameter; about 40 nm pore diameter; about 50 nm pore diameter; about 55 nm pore diameter; about 60 nm pore diameter; about 65 nm pore diameter; about 70 nm pore diameter; about 75 nm pore diameter; about 80 nm pore diameter; about 85 nm pore diameter; about 90 nm pore diameter; about 95 nm pore diameter; about 100 nm pore diameter; about 105 nm pore diameter; about 110 nm pore diameter; about 115 nm pore diameter; about 120 nm pore diameter; about 125 nm pore diameter; about 130 nm pore diameter; about 135 nm pore diameter; about 140 nm pore diameter; about 145 nm pore diameter; about 150 nm pore diameter; about 155 nm pore diameter; about 160 nm pore diameter; about 165 nm pore diameter; about 170 nm pore diameter; about 175 nm pore diameter; about 180 nm pore diameter; about 185 nm pore diameter; about 190 nm pore diameter; about 195 nm pore diameter; about 200 nm pore diameter; about 205 nm pore diameter; about 210 nm pore diameter; about 215 nm pore diameter; about 220 nm pore diameter; about 225 nm pore diameter; about 230 nm pore diameter; about 235 nm pore diameter; about 240 nm pore diameter; about 245 nm pore diameter; about 250 nm pore diameter; about 255 nm pore diameter; about 260 nm pore diameter; about 265 nm pore diameter; about 270 nm pore diameter; about 275 nm pore diameter; about 280 nm pore diameter; about 285 nm pore diameter; about 290 nm pore diameter; about 295 nm pore diameter; about 300 nm pore diameter; about 305 nm pore diameter; about 310 nm pore diameter; about 315 nm pore diameter; about 320 nm pore diameter; about 320 nm pore diameter; about 330 nm pore diameter; about 335 nm pore diameter; about 340 nm pore diameter; about 345 nm pore diameter; about 350 nm pore diameter; about 355 nm pore diameter; about 360 nm pore diameter; about 365 nm pore diameter; about 370 nm pore diameter; about 375 nm pore diameter; about 380 nm pore diameter; about 390 nm pore diameter; about 400 nm pore diameter; about 410 nm pore diameter; about 420 nm pore diameter; about 430 nm pore diameter; about 440 nm pore diameter; about 450 nm pore diameter; about 460 nm pore diameter; about 470 nm pore diameter; about 480 nm pore diameter; about 490 nm pore diameter; about 500 nm pore diameter; about 600 nm pore diameter; about 700 nm pore diameter; about 800 nm pore diameter; about 900 nm pore diameter; about 1000 nm pore diameter; about 1100 nm pore diameter; about 1200 nm pore diameter; about 1300 nm pore diameter; about 1400 nm pore diameter; about 1500 nm pore diameter; about 1600 nm pore diameter; about 1700 nm pore diameter; about 1800 nm pore diameter; about 1900 nm pore diameter; about 2000 nm pore diameter; about 2100 nm pore diameter; about 2200 nm pore diameter; about 2300 nm pore diameter; about 2400 nm pore diameter; about 2500 nm pore diameter; about 2600 nm pore diameter; about 2700 nm pore diameter; about 2800 nm pore diameter; about 2900 nm pore diameter; about 3000 nm pore diameter; about 3100 nm pore diameter; about 3200 nm pore diameter; about 3300 nm pore diameter; about 3400 nm pore diameter; or about 3500 nm pore diameter. It is understood that recitation of the above discrete values includes a range between each recited value.

The mineral coating, as described herein, can include a ratio of at least about 0.1 Ca/P. For example, the mineral coating can include a ratio of at least about 0.1 Ca/P; at least about 0.2 Ca/P; at least about 0.3 Ca/P; at least about 0.4 Ca/P; at least about 0.5 Ca/P; at least about 0.6 Ca/P; at least about 0.7 Ca/P; at least about 0.8 Ca/P; at least about 0.9 Ca/P; at least about 1.0 Ca/P; at least about 1.1 Ca/P; at least about 1.2 Ca/P; at least about 1.3 Ca/P; at least about 1.4 Ca/P; at least about 1.5 Ca/P; at least about 1.6 Ca/P; at least about 1.7 Ca/P; at least about 1.8 Ca/P; at least about 1.9 Ca/P; at least about 2.0 Ca/P; at least about 2.1 Ca/P; at least about 2.2 Ca/P; at least about 2.3 Ca/P; at least about 2.4 Ca/P; at least about 2.5 Ca/P; at least about 2.6 Ca/P; at least about 2.7 Ca/P; at least about 2.8 Ca/P; at least about 2.9 Ca/P; at least about 3.0 Ca/P; at least about 3.1 Ca/P; at least about 3.2 Ca/P; at least about 3.3 Ca/P; at least about 3.4 Ca/P; at least about 3.5 Ca/P; at least about 3.6 Ca/P; at least about 3.7 Ca/P; at least about 3.8 Ca/P; at least about 3.9 Ca/P; at least about 4 Ca/P; at least about 5 Ca/P; at least about 6 Ca/P; at least about 7 Ca/P; at least about 8 Ca/P; at least about 9 Ca/P; at least about 10 Ca/P; at least about 11 Ca/P; at least about 12 Ca/P; at least about 13 Ca/P; at least about 14 Ca/P; at least about 15 Ca/P; at least about 16 Ca/P; at least about 17 Ca/P; at least about 18 Ca/P; at least about 19 Ca/P; or at least about 20 Ca/P. It is understood that recitation of the above discrete values includes a range between each recited value.

As another example, the mineral coating can include a ratio of about 0.1 Ca/P, about 0.2 Ca/P, about 0.3 Ca/P, about 0.4 Ca/P, about 0.5 Ca/P, about 0.6 Ca/P, about 0.7 Ca/P, about 0.8 Ca/P, about 0.9 Ca/P, about 1.0 Ca/P, about 1.1 Ca/P, about 1.2 Ca/P, about 1.3 Ca/P, about 1.4 Ca/P, about 1.5 Ca/P, about 1.6 Ca/P, about 1.7 Ca/P, about 1.8 Ca/P, about 1.9 Ca/P, about 2.0 Ca/P, about 2.1 Ca/P, about 2.2 Ca/P, about 2.3 Ca/P, about 2.4 Ca/P, about 2.5 Ca/P, about 2.6 Ca/P, about 2.7 Ca/P, about 2.8 Ca/P, about 2.9 Ca/P, about 3.0 Ca/P, about 3.1 Ca/P, about 3.2 Ca/P, about 3.3 Ca/P, about 3.4 Ca/P, about 3.5 Ca/P, about 3.6 Ca/P, about 3.7 Ca/P, about 3.8 Ca/P, about 3.9 Ca/P, about 4 Ca/P, about 5 Ca/P, about 6 Ca/P, about 7 Ca/P, about 8 Ca/P, about 9 Ca/P, about 10 Ca/P, about 11 Ca/P, about 12 Ca/P, about 13 Ca/P, about 14 Ca/P, about 15 Ca/P, about 16 Ca/P, about 17 Ca/P, about 18 Ca/P, about 19 Ca/P, or about 20 Ca/P. It is understood that recitation of the above discrete values includes a range between each recited value.

A mineral coating, as described herein, can be characterized by conventional methods. For example, mineral formation in mSBF can be tracked by analyzing changes in solution calcium concentration using a calcium sensitive electrode (Denver Instrument, Denver, Colo.). After their growth, the mineral matrices can be dissolved and analyzed for calcium and phosphate ion content to quantify mineral formation, and the mineral crystals can be analyzed morphologically and compositionally using a scanning electron microscope (SEM), e.g., with a Noran SiLi detector for elemental analysis.

For example, the crystalline phase can be characterized by X-ray diffraction, where 2θ is in the range of 15-35° or 25.8°, 28.1°, 28.9°, 31.8°, or 32.1°.

As another example, as described herein, the chemical composition or crystalline phase can be characterized by Fourier transform infrared spectroscopy (FTIR), where carbonate peaks can be in the 1400-1500 cm-1 region and phosphate peaks can be in the 900-1100 cm-1 region or about 570 cm-1, 962 cm-1, or 1050 cm.

As another example, as described herein, dissolution of mineral layers can also be characterized by measuring release of calcium and phosphate ions during incubation in tris-buffered saline at physiologically relevant conditions (e.g., 37° C., pH 7.4).

As another example, as described herein, calcium and phosphate concentrations can be measured using previously described colorimetric assays (see Murphy et al., "Bi16 inspired growth of crystalline carbonate apatite on biodegradable polymer substrata", J Am Chem Soc 124:1910-7,2002). Each of the characterization methods described herein are routine in analysis of inorganic materials and is consistent with FDA's good guidance practices for design and testing of calcium phosphate coatings (see Devices FDoGaR. Calcium phosphate coating draft guidance for preparation of FDA submissions for orthopedic and dental endosseous implants. 1997).

As another example, as described herein, the mineral coating, can be predominantly crystalline, but can be present in amorphous forms. For example, the mineral coating can have at least about 5% crystallinity. For example, a mineral coating can include at least about 5% crystallinity; at least about 10% crystallinity; at least about 15% crystallinity; at least about 20% crystallinity; at least about 25% crystallinity; at least about 30% crystallinity; at least about 35% crystallinity; at least about 40% crystallinity; at least about 45% crystallinity; at least about 46% crystallinity; at least about 47% crystallinity; at least about 48% crystallinity; at least about 49% crystallinity; at least about 50% crystallinity; at least about 51% crystallinity; at least about 52% crystallinity; at least about 53% crystallinity; at least about 54% crystallinity; at least about 55% crystallinity; at least about 56% crystallinity; at least about 57% crystallinity; at least about 58% crystallinity; at least about 59% crystallinity; at least about 60% crystallinity; at least about 61% crystallinity; at least about 62% crystallinity; at least about 63% crystallinity; at least about 64% crystallinity; at least about 65% crystallinity; at least about 66% crystallinity; at least about 67% crystallinity; at least about 68% crystallinity; at least about 69% crystallinity; at least about 70% crystallinity; at least about 71% crystallinity; at least about 72% crystallinity; at least about 73% crystallinity; at least about 74% crystallinity; at least about 75% crystallinity; at least about 76% crystallinity; at least about 77% crystallinity; at least about 78% crystallinity; at least about 79% crystallinity; at least about 80% crystallinity; at least about 81% crystallinity; at least about 82% crystallinity; at least about 83% crystallinity; at least about 84% crystallinity; at least about 85% crystallinity; at least about 86% crystallinity; at least about 87% crystallinity; at least about 88% crystallinity; at least about 89% crystallinity; at least about 90% crystallinity; at least about 91% crystallinity; at least about 92% crystallinity; at least about 93% crystallinity; at least about 94% crystallinity; at least about 95% crystallinity; at least about 96% crystallinity; at least about 97% crystallinity; at least about 98% crystallinity; at least about 99% crystallinity; or at least about 100% crystallinity. It is understood that recitation of the above discrete values includes a range between each recited value.

As another example, a mineral coating can include about 5% crystallinity; 10% crystallinity; about 15% crystallinity; about 20% crystallinity; about 25% crystallinity; about 30% crystallinity; about 35% crystallinity; about 40% crystallinity; about 45% crystallinity; about 46% crystallinity; about 47% crystallinity; about 48% crystallinity; about 49% crystallinity; about 50% crystallinity; about 51% crystallinity; about 52% crystallinity; about 53% crystallinity; about 54% crystallinity; about 55% crystallinity; about 56% crystallinity; about 57% crystallinity; about 58% crystallinity; about 59% crystallinity; about 60% crystallinity; about 61% crystallinity; about 62% crystallinity; about 63% crystallinity; about 64% crystallinity; about 65% crystallinity; about 66% crystallinity; about 67% crystallinity; about 68% crystallinity; about 69% crystallinity; about 70% crystallinity; about 71% crystallinity; about 72% crystallinity; about 73% crystallinity; about 74% crystallinity; about 75% crystallinity; about 76% crystallinity; about 77% crystallinity; about 78% crystallinity; about 79% crystallinity; about 80% crystallinity; about 81% crystallinity; about 82% crystallinity; about 83% crystallinity; about 84% crystallinity; about 85% crystallinity; about 86% crystallinity; about 87% crystallinity; about 88% crystallinity; about 89% crystallinity; about 90% crystallinity; about 91% crystallinity; about 92% crystallinity; about 93% crystallinity; about 94% crystallinity; about 95% crystallinity; about 96% crystallinity; about 97% crystallinity; about 98% crystallinity; about 99% crystallinity; or about 100% crystallinity. It is understood that recitation of the above discrete values includes a range between each recited value.

In some embodiments, the coated bone material is comprising, consisting essentially of, or consisting of a plurality of porous macroparticles lyophilized into a rectangular shape prepared from ceramic material and embedded in a matrix of collagen. The plurality of porous macroparticles are coated with a mineral coating. The mineral coating comprises, consists essentially of, or consists of a carbonated calcium-deficient hydroxyapatite component. The bone material also comprises a plurality of surface markers, for example, recesses, projections, or a combination thereof. In some embodiments, as illustrated in FIG. 8, the bone material includes one or more channels 316 (which are recesses) which not only serve as surface markers but also increase the surface area and hydration characteristics of the bone material. In some embodiments, channels are recesses that can have a macro half-cylindrical shape. In other embodiments, channels can have other shapes, for example, a trapezoidal or square shape, that can be easily identifiable under visible light. In some embodiments, hydration channel can have a 1 mm diameter.

In various embodiments, the plurality of lyophilized porous macroparticles may include, but are not limited to, MasterGraft® Strip produced by Medtronic Sofamor Danek, Inc., Memphis, Tenn.; MasterGraft® Putty produced by Medtronic Sofamor Danek, Inc., Memphis, Tenn., and Matrix EXT compression resistant products produced by Medtronic Sofamor Danek, Inc., Memphis, Tenn.

In other embodiments, the lyophilized porous macroparticles are coated with a mineral coating which comprises, consists essentially of, or consists of a plate-like nanostructure including a carbonate-substituted, calcium-deficient hydroxyapatite component. These mineral coatings are like bone and have been found to stimulate bone cells creating an enhanced cellular environment for bone healing. In these embodiments, the lyophilized porous macroparticles whether they are or are not coated can be formed into strips or other resorbable osteoconductive cohesive scaffolds. While easily discernable under scanning electron microscope (SEM), the strips or scaffolds coated with the mineral coating are not readily distinguished under visible light. In sum, to the naked eye, whether the strips are or are not coated, visually, they may appear identical. It has also been found unexpectedly that the surface markers used to texturize the coated macroparticles serve not only to differentiate between coated and uncoated grafts but also increase the surface area of the coated macroparticles, exhibit increasing hydration characteristics and enhanced mechanical characteristics of a resulting bone material allowing for improved biological integration into a selected surgical site. For example, while the surface area of a MasterGraft® granule is from about 0.3 to about 0.5 $m^2/g$, the surface area of a MasterGraft® granule coated with a mineral coating comprising nanoparticles having carbonate substituted, calcium-deficient hydroxyapatite including surface markers provides an increase in surface area of from about 300 to about 500% to a surface area of from about 2, 3, 4, 5 $m^2/g$, 6, 7, 8, 9, 10, 15, 20, 25, 30, 35, 40, 45, 50, 55, 60, 65, 70, 75, 80, 85, 90, 95 to about 100 $m^2/g$.

In various embodiments, the surface markers include, without limitation, macro texture features formed by applying texture patterns to one side of the bone material formed in the mold surface or by cutting and etching texture patterns on most surfaces of the bone material after lyophilization. These designs can be the macro structures in patterns of recesses and/or projections of a variety of shapes. In some embodiments, macro surface markers include a plurality of recesses, projections, or a combination thereof, for example, squared or curved surfaces and various types of engineered notches. In various embodiments, the recesses, projections, or combinations thereof form a pattern or random shapes. In some aspects, the recesses, projections or combinations thereof form square, cylindrical, corrugated, notched, curved, waffle, hexagonal or honeycomb or oval shapes in the mineral coated bone material. In other embodiments, the plurality of recesses, projections or combinations thereof are radiographic markers, hydration channels, or indicia to determine bone growth within or bone growth adjacent to the bone material. It will be understood that the surface markers can have an alternating pattern (e.g., circles alternating with squares, etc.) or can be disposed throughout the material randomly in a non-uniform pattern.

In various embodiments, bone implants prepared of uncoated MasterGraft®, for example, can contain micropores of about 500 µm. The addition of a mineral coating having micropores increases the surface area of MasterGraft® bone implant and enhances the dissolution rate of $Ca^{2+}$ and $PO_{4-}$. As a result of the increase in the dissolution rate of $Ca^{2+}$ and $PO_{4-}$ new mineral deposition of bone material increases. Further, micron-sized grains may be removed following cell-mediated resorption. In various embodiments, other kinds of bone material can be mineral coated with coatings having surface markers as described in this application.

In other embodiments, bone materials are coated with mineralized coatings having a plate-like nanostructure of carbonate substituted, calcium-deficient hydroxyapatite (HA/TCP) The resulting nanopore size varies from about 0.1 µm to about 0.2 µm. In these embodiments, the nano morphology of the mineral coating increases the specific surface are of the bone implant and as a result it stimulates bone cell growth. In addition, the increased surface area further enhances early-stage dissolution increasing the availability of $Ca^{2+}$ and $PO_{4-}$, thus increasing new mineral deposition. In several aspects, the bone material has pores (i) from about 50 µm to about 500 µm for bone growth or (ii) from about 500 µm to about 5 mm for vascularization.

A modified simulated body fluid as described herein can be used to mineral coat a scaffold. For example, the scaffold can be immersed and incubated in a modified simulated body fluid. As another example, the modified simulated body fluid can be replaced, replenished, or removed and added at least about once a day; at least about twice per day; or at least about three times per day. As another example, the modified simulated body fluid can be replaced at least about once every day; at least about once every two days; at least once every three days; at least once every four days; at least once every five days; at least once every six days; or at least once every seven days.

As described herein, a modified simulated body fluid can be a solution of ionic constituents of blood plasma, with double the concentrations of calcium and phosphate ions.

As described herein, a modified simulated body fluid can be a solution comprising NaCl, KCl, MgCl2, MgSO4, NaHCO3, CaCl2, and KH2PO4.

A modified simulated body fluid can include at least about 1 mM NaCl. For example, a modified simulated body fluid can include at least about 1 mM NaCl; at least about 10 mM NaCl; at least about 20 mM NaCl; at least about 30 mM NaCl; at least about 40 mM NaCl; at least about 50 mM NaCl; at least about 60 mM NaCl; at least about 70 mM NaCl; at least about 80 mM NaCl; at least about 90 mM NaCl; at least about 100 mM NaCl; at least about 110 mM NaCl; at least about 120 mM NaCl; at least about 130 mM NaCl; at least about 140 mM NaCl; at least about 150 mM NaCl; at least about 160 mM NaCl; at least about 170 mM NaCl; at least about 180 mM NaCl; at least about 190 mM NaCl; at least about 200 mM NaCl; at least about 300 mM NaCl; at least about 400 mM NaCl; at least about 500 mM NaCl; at least about 600 mM NaCl; at least about 700 mM NaCl; at least about 800 mM NaCl; at least about 900 mM NaCl; at least about 1000 mM NaCl; at least about 1100 mM NaCl; at least about 1200 mM NaCl; at least about 1300 mM NaCl; at least about 1400 mM NaCl; at least about 1500 mM NaCl; at least about 1600 mM NaCl; at least about 1700 mM NaCl; at least about 1800 mM NaCl; at least about 1900 mM NaCl; or at least about 2000 mM NaCl. It is understood that recitation of the above discrete values includes a range between each recited value.

As another example, a modified simulated body fluid can include about 1 mM NaCl, about 10 mM NaCl; about 20 mM NaCl; about 30 mM NaCl; about 40 mM NaCl; about 50 mM NaCl; about 60 mM NaCl; about 70 mM NaCl; about 80 mM NaCl; about 90 mM NaCl; about 100 mM NaCl; about 110 mM NaCl; about 120 mM NaCl; about 130 mM NaCl; about 140 mM NaCl; about 150 mM NaCl; about 160 mM NaCl; about 170 mM NaCl; about 180 mM NaCl; about 190 mM NaCl; about 200 mM NaCl; about 300 mM NaCl; about 400 mM NaCl; about 500 mM NaCl; about 600 mM NaCl; about 700 mM NaCl; about 800 mM NaCl; about 900 mM NaCl; about 1000 mM NaCl; about 1100 mM NaCl; about 1200 mM NaCl; about 1300 mM NaCl; about 1400 mM NaCl; about 1500 mM NaCl; about 1600 mM NaCl; about 1700 mM NaCl; about 1800 mM NaCl; about 1900 mM NaCl; or about 2000 mM NaCl. It is understood that recitation of the above discrete values includes a range between each recited value.

A modified simulated body fluid can include at least about 0.4 mM KCl. For example, a modified simulated body fluid can include at least about 0.4 mM KCl; at least about 1 mM KCl; at least about 2 mM KCl; at least about 3 mM KCl; at least about 4 mM KCl; at least about 5 mM KCl; at least about 6 mM KCl; at least about 7 mM KCl; at least about 8 mM KCl; at least about 9 mM KCl; at least about 10 mM KCl; at least about 11 mM KCl; at least about 12 mM KCl; at least about 13 mM KCl; at least about 14 mM KCl; at least about 15 mM KCl; at least about 16 mM KCl; at least about 17 mM KCl; at least about 18 mM KCl; at least about 19 mM KCl; at least about 20 mM KCl; at least about 21 mM KCl; at least about 22 mM KCl; at least about 23 mM KCl; at least about 24 mM KCl; at least about 25 mM KCl; at least about 26 mM KCl; at least about 27 mM KCl; at least about 28 mM KCl; at least about 29 mM KCl; at least about 30 mM KCl; at least about 31 mM KCl; at least about 32 mM KCl; at least about 33 mM KCl; at least about 34 mM KCl; at least about 35 mM KCl; at least about 36 mM KCl; at least about 37 mM KCl; at least about 38 mM KCl; at least about 39 mM KCl; at least about 40 mM KCl; at least about 41 mM KCl; at least about 42 mM KCl; at least about 43 mM KCl; at least about 44 mM KCl; at least about 45 mM KCl; at least about 46 mM KCl; at least about 47 mM KCl; at least about 48 mM KCl; at least about 49 mM KCl; at least about 50 mM KCl; at least about 51 mM KCl; at least about 52 mM KCl; at least about 53 mM KCl; at least about 54 mM KCl; at least about 55 mM KCl; at least about 56 mM KCl; at least about 57 mM KCl; at least about 58 mM KCl; at least about 59 mM KCl; at least about 60 mM KCl; at least about 61 mM KCl; at least about 62 mM KCl; at least about 63 mM KCl; at least about 64 mM KCl; at least about 65 mM KCl; at least about 66 mM KCl; at least about 67 mM KCl; at least about 68 mM KCl; at least about 69 mM KCl; at least about 70 mM KCl; at least about 71 mM KCl; at least about 72 mM KCl; at least about 73 mM KCl; at least about 74 mM KCl; at least about 75 mM KCl; at least about 76 mM KCl; at least about 77 mM KCl; at least about 78 mM KCl; at least about 79 mM KCl; or at least about 80 mM KCl. It is understood that recitation of the above discrete values includes a range between each recited value.

As another example, a modified simulated body fluid can include about 0.4 mM KCl, about 1 mM KCl, about 2 mM KCl, about 3 mM KCl, about 4 mM KCl, about 5 mM KCl, about 6 mM KCl, about 7 mM KCl, about 8 mM KCl, about 9 mM KCl, about 10 mM KCl, about 11 mM KCl, about 12 mM KCl, about 13 mM KCl, about 14 mM KCl, about 15 mM KCl, about 16 mM KCl, about 17 mM KCl, about 18 mM KCl, about 19 mM KCl, about 20 mM KCl, about 21 mM KCl, about 22 mM KCl, about 23 mM KCl, about 24 mM KCl, about 25 mM KCl, about 26 mM KCl, about 27 mM KCl, about 28 mM KCl, about 29 mM KCl, about 30 mM KCl, about 31 mM KCl, about 32 mM KCl, about 33 mM KCl, about 34 mM KCl, about 35 mM KCl, about 36 mM KCl, about 37 mM KCl, about 38 mM KCl, about 39 mM KCl, about 40 mM; about 41 mM KCl, about 42 mM KCl, about 43 mM KCl, about 44 mM KCl, about 45 mM KCl, about 46 mM KCl, about 47 mM KCl, about 48 mM KCl, about 49 mM KCl, about 50 mM KCl, about 51 mM KCl, about 52 mM KCl, about 53 mM KCl, about 54 mM KCl, about 55 mM KCl, about 56 mM KCl, about 57 mM KCl, about 58 mM KCl, about 59 mM KCl, about 60 mM KCl, about 61 mM KCl, about 62 mM KCl, about 63 mM KCl, about 64 mM KCl, about 65 mM KCl, about 66 mM KCl, about 67 mM KCl, about 68 mM KCl, about 69 mM KCl, about 70 mM KCl, about 71 mM KCl, about 72 mM KCl, about 73 mM KCl, about 74 mM KCl, about 75 mM KCl, about 76 mM KCl, about 77 mM KCl, about 78 mM KCl, about 79 mM KCl, or about 80 mM KCl. It is understood that recitation of the above discrete values includes a range between each recited value.

A modified simulated body fluid can include at least about 0.1 mM $MgCl_2$. For example, a modified simulated body fluid can include at least about 0.1 mM $MgCl_2$, at least about 0.25 mM $MgCl_2$, at least about 0.5 mM $MgCl_2$, at least about 1 mM $MgCl_2$, at least about 1.25 mM $MgCl_2$, at least about 1.5 mM $MgCl_2$, at least about 1.75 mM $MgCl_2$, at least about 2 mM $MgCl_2$, at least about 2.25 mM $MgCl_2$, at least about 2.5 mM $MgCl_2$, at least about 2.75 mM $MgCl_2$, at least about 3 mM $MgCl_2$, at least about 3.25 mM $MgCl_2$, at least about 3.5 mM $MgCl_2$, at least about 3.75 mM $MgCl_2$, at least about 4 mM $MgCl_2$, at least about 4.25 mM $MgCl_2$, at least about 4.5 mM $MgCl_2$, at least about 4.75 mM $MgCl_2$, at least about 5 mM $MgCl_2$, at least about 5.25 mM $MgCl_2$, at least about 5.5 mM $MgCl_2$, at least about 5.75 mM $MgCl_2$, at least about 6 mM $MgCl_2$, at least about 6.25 mM $MgCl_2$, at least about 6.5 mM $MgCl_2$, at least about 6.75 mM $MgCl_2$, at least about 7 mM $MgCl_2$, at least about 7.25 mM $MgCl_2$, at least about 7.5 mM $MgCl_2$, at least about 7.75 mM $MgCl_2$, at least about 8 mM $MgCl_2$, at least about 8.25 mM $MgCl_2$, at least about 8.5 mM $MgCl_2$, at least about 8.75 mM $MgCl_2$, at least about 9 mM $MgCl_2$, at least about 9.25 mM $MgCl_2$, at least about 9.5 mM $MgCl_2$, at least about 9.75 mM $MgCl_2$, at least about 10 mM $MgCl_2$, at least about 11 mM $MgCl_2$, at least about 12 mM $MgCl_2$, at least about 13 mM $MgCl_2$, at least about 14 mM $MgCl_2$, at least about 15 mM $MgCl_2$, at least about 16 mM $MgCl_2$, at least about 17 mM $MgCl_2$, at least about 18 mM $MgCl_2$, at least about 19 mM $MgCl_2$, at least about 20 mM $MgCl_2$, at least about 21 mM $MgCl_2$, at least about 22 mM $MgCl_2$, at least about 23 mM $MgCl_2$, at least about 24 mM $MgCl_2$, at least about 25 mM $MgCl_2$, at least about 26 mM $MgCl_2$, at least about 27 mM $MgCl_2$, at least about 28 mM $MgCl_2$, at least about 29 mM $MgCl_2$, at least about 30 mM $MgCl_2$, at least about 31 mM $MgCl_2$, at least about 32 mM $MgCl_2$, at least about 33 mM $MgCl_2$, at least about 34 mM $MgCl_2$, at least about 35 mM $MgCl_2$, at least about 36 mM $MgCl_2$, at least about 37 mM $MgCl_2$, at least about 38 mM $MgCl_2$, at least about 39 mM $MgCl_2$, at least about 40 mM $MgCl_2$, at least about 41 mM $MgCl_2$, at least about 42 mM $MgCl_2$, at least about 43 mM $MgCl_2$, at least about 44 mM $MgCl_2$, at least about 45 mM $MgCl_2$, at least about 46 mM $MgCl_2$, at least about 47 mM $MgCl_2$, at least about 48 mM $MgCl_2$, at least about 49 mM $MgCl_2$, or at least about 50 mM $MgCl_2$. It is understood that recitation of the above discrete values includes a range between each recited value.

As another example, a modified simulated body fluid can include about 0.1 mM $MgCl_2$, at least about 0.25 mM $MgCl_2$, about 0.5 mM $MgCl_2$, about 1 mM $MgCl_2$, about 1.25 mM $MgCl_2$, about 1.5 mM $MgCl_2$, about 1.75 mM $MgCl_2$, about 2 mM $MgCl_2$, about 2.25 mM $MgCl_2$, about 2.5 mM $MgCl_2$, about 2.75 mM $MgCl_2$, about 3 mM $MgCl_2$, about 3.25 mM $MgCl_2$, about 3.5 mM $MgCl_2$, about 3.75 mM $MgCl_2$, about 4 mM $MgCl_2$, about 4.25 mM $MgCl_2$, about 4.5 mM $MgCl_2$, about 4.75 mM $MgCl_2$, about 5 mM $MgCl_2$, about 5.25 mM $MgCl_2$, about 5.5 mM $MgCl_2$, about 5.75 mM $MgCl_2$, about 6 mM $MgCl_2$, about 6.25 mM $MgCl_2$, about 6.5 mM $MgCl_2$, about 6.75 mM $MgCl_2$, about 7 mM $MgCl_2$, about 7.25 mM $MgCl_2$, about 7.5 mM $MgCl_2$, about 7.75 mM $MgCl_2$, about 8 mM $MgCl_2$, about 8.25 mM $MgCl_2$, about 8.5 mM $MgCl_2$, about 8.75 mM $MgCl_2$, about 9 mM $MgCl_2$, about 9.25 mM $MgCl_2$, about 9.5 mM $MgCl_2$, about 9.75 mM $MgCl_2$, about 10 mM $MgCl_2$, about 11 mM $MgCl_2$, about 12 mM $MgCl_2$, about 13 mM $MgCl_2$, about 14 mM $MgCl_2$, about 15 mM $MgCl_2$, about 16 mM $MgCl_2$, about 17 mM $MgCl_2$, about 18 mM $MgCl_2$, about 19 mM $MgCl_2$, about 20 mM $MgCl_2$, about 21 mM $MgCl_2$, about 22 mM $MgCl_2$, about 23 mM $MgCl_2$, about 24 mM $MgCl_2$, about 25 mM $MgCl_2$, about 26 mM $MgCl_2$, about 27 mM $MgCl_2$, about 28 mM $MgCl_2$, about 29 mM $MgCl_2$, about 30 mM $MgCl_2$, about 31 mM $MgCl_2$, about 32 mM $MgCl_2$, about 33 mM $MgCl_2$, about 34 mM $MgCl_2$, about 35 mM $MgCl_2$, about 36 mM $MgCl_2$, about 37 mM $MgCl_2$, about 38 mM $MgCl_2$, about 39 mM $MgCl_2$, about 40 mM $MgCl_2$, about 41 mM $MgCl_2$, about 42 mM $MgCl_2$, about 43 mM $MgCl_2$, about 44 mM $MgCl_2$, about 45 mM $MgCl_2$, about 46 mM $MgCl_2$, about 47 mM $MgCl_2$, about 48 mM $MgCl_2$, about 49 mM $MgCl_2$, or about 50 mM $MgCl_2$. It is understood that recitation of the above discrete values includes a range between each recited value.

A modified simulated body fluid can include at least about 0.05 mM $MgSO_4$. For example, a modified simulated body fluid can include at least about 0.05 mM $MgSO_4$; at least about 0.25 mM $MgSO_4$; at least about 0.5 mM $MgSO_4$; at least about 0.75 mM $MgSO_4$; at least about 1 mM $MgSO_4$; at least about 1.25 mM $MgSO_4$; at least about 1.5 mM $MgSO_4$; at least about 1.75 mM $MgSO_4$; at least about 2 mM $MgSO_4$; at least about 2.25 mM $MgSO_4$; at least about 2.5 mM $MgSO_4$; at least about 2.75 mM $MgSO_4$; at least about 3 mM $MgSO_4$; at least about 3.25 mM $MgSO_4$; at least about 3.5 mM $MgSO_4$; at least about 3.75 mM $MgSO_4$; at least about 4 mM $MgSO_4$; at least about 4.25 mM $MgSO_4$; at least about 4.5 mM $MgSO_4$; at least about 4.75 mM $MgSO_4$; at least about 5 mM $MgSO_4$; at least about 6 mM $MgSO_4$; at least about 7 mM $MgSO_4$; at least about 8 mM $MgSO_4$; at least about 9 mM $MgSO_4$; at least about 10 mM $MgSO_4$; at least about 11 mM $MgSO_4$; at least about 12 mM $MgSO_4$; at least about 13 mM $MgSO_4$; at least about 14 mM $MgSO_4$; at least about 15 mM $MgSO_4$; at least about 16 mM $MgSO_4$; at least about 17 mM $MgSO_4$; at least about 18 mM $MgSO_4$; at least about 19 mM $MgSO_4$; at least about 20 mM $MgSO_4$; at least about 21 mM $MgSO_4$; at least about 22 mM $MgSO_4$; at least about 23 mM $MgSO_4$; at least about 24 mM $MgSO_4$; at least about 25 mM $MgSO_4$; at least about 26 mM $MgSO_4$; at least about 27 mM $MgSO_4$; at least about 28 mM $MgSO_4$; at least about 29 mM $MgSO_4$; at least about 30 mM $MgSO_4$; at least about 31 mM $MgSO_4$; at least about 32 mM $MgSO_4$; at least about 33 mM $MgSO_4$; at least about 34 mM $MgSO_4$; at least about 35 mM $MgSO_4$; at least about 36 mM $MgSO_4$; at least about 37 mM $MgSO_4$; at least about 38 mM $MgSO_4$;

at least about 39 mM $MgSO_4$; at least about 40 mM $MgSO_4$; at least about 41 mM $MgSO_4$; at least about 42 mM $MgSO_4$; at least about 43 mM $MgSO_4$; at least about 44 mM $MgSO_4$; at least about 45 mM $MgSO_4$; at least about 46 mM $MgSO_4$; at least about 47 mM $MgSO_4$; at least about 48 mM $MgSO_4$; at least about 49 mM $MgSO_4$; or at least about 50 mM $MgSO_4$. It is understood that recitation of the above discrete values includes a range between each recited value.

As another example, a modified simulated body fluid can include about 0.05 mM $MgSO_4$; about 0.25 mM $MgSO_4$; about 0.5 mM $MgSO_4$; about 0.75 mM $MgSO_4$; about 1 mM $MgSO_4$; about 1.25 mM $MgSO_4$; about 1.5 mM $MgSO_4$; about 1.75 mM $MgSO_4$; about 2 mM $MgSO_4$; about 2.25 mM $MgSO_4$; about 2.5 mM $MgSO_4$; about 2.75 mM $MgSO_4$; about 3 mM $MgSO_4$; about 3.25 mM $MgSO_4$; about 3.5 mM $MgSO_4$; about 3.75 mM $MgSO_4$; about 4 mM $MgSO_4$; about 4.25 mM $MgSO_4$; about 4.5 mM $MgSO_4$; about 4.75 mM $MgSO_4$; about 5 mM $MgSO_4$; about 6 mM $MgSO_4$; about 7 mM $MgSO_4$; about 8 mM $MgSO_4$; about 9 mM $MgSO_4$; about 10 mM $MgSO_4$; about 11 mM $MgSO_4$; about 12 mM $MgSO_4$; about 13 mM $MgSO_4$; about 14 mM $MgSO_4$; about 15 mM $MgSO_4$; about 16 mM $MgSO_4$; about 17 mM $MgSO_4$; about 18 mM $MgSO_4$; about 19 mM $MgSO_4$; about 20 mM $MgSO_4$; about 21 mM $MgSO_4$; about 22 mM $MgSO_4$; about 23 mM $MgSO_4$; about 24 mM $MgSO_4$; about 25 mM $MgSO_4$; about 26 mM $MgSO_4$; about 27 mM $MgSO_4$; about 28 mM $MgSO_4$; about 29 mM $MgSO_4$; about 30 mM $MgSO_4$; about 31 mM $MgSO_4$; about 32 mM $MgSO_4$; about 33 mM $MgSO_4$; about 34 mM $MgSO_4$; about 35 mM $MgSO_4$; about 36 mM $MgSO_4$; about 37 mM $MgSO_4$; about 38 mM $MgSO_4$; about 39 mM $MgSO_4$; about 40 mM $MgSO_4$; about 41 mM $MgSO_4$; about 42 mM $MgSO_4$; about 43 mM $MgSO_4$; about 44 mM $MgSO_4$; about 45 mM $MgSO_4$; about 46 mM $MgSO_4$; about 47 mM $MgSO_4$; about 48 mM $MgSO_4$; about 49 mM $MgSO_4$; or about 50 mM $MgSO_4$. It is understood that recitation of the above discrete values includes a range between each recited value.

A modified simulated body fluid can include at least about 0.4 mM $NaHCO_3$. For example, a modified simulated body fluid can include at least about 0.4 mM $NaHCO_3$; at least about 0.6 mM $NaHCO_3$; at least about 0.8 mM $NaHCO_3$; at least about 1.0 mM $NaHCO_3$; at least about 1.2 mM $NaHCO_3$; at least about 1.4 mM $NaHCO_3$; at least about 1.6 mM $NaHCO_3$; at least about 1.8 mM $NaHCO_3$; at least about 2.0 mM $NaHCO_3$; at least about 2.2 mM $NaHCO_3$; at least about 2.4 mM $NaHCO_3$; at least about 2.6 mM $NaHCO_3$; at least about 2.8 mM $NaHCO_3$; at least about 3.0 mM $NaHCO_3$; at least about 3.2 mM $NaHCO_3$; at least about 3.4 mM $NaHCO_3$; at least about 3.6 mM $NaHCO_3$; at least about 3.8 mM $NaHCO_3$; at least about 4.0 mM $NaHCO_3$; at least about 4.2 mM $NaHCO_3$; at least about 4.4 mM $NaHCO_3$; at least about 4.6 mM $NaHCO_3$; at least about 4.8 mM $NaHCO_3$; at least about 5.0 mM $NaHCO_3$; at least about 5.2 mM $NaHCO_3$; at least about 5.4 mM $NaHCO_3$; at least about 5.6 mM $NaHCO_3$; at least about 5.8 mM $NaHCO_3$; at least about 6.0 mM $NaHCO_3$; at least about 6.2 mM $NaHCO_3$; at least about 6.4 mM $NaHCO_3$; at least about 6.6 mM $NaHCO_3$; at least about 6.8 mM $NaHCO_3$; at least about 7.0 mM $NaHCO_3$; at least about 7.2 mM $NaHCO_3$; at least about 7.4 mM $NaHCO_3$; at least about 7.6 mM $NaHCO_3$; at least about 7.8 mM $NaHCO_3$; at least about 8.0 mM $NaHCO_3$; at least about 8.2 mM $NaHCO_3$; at least about 8.4 mM $NaHCO_3$; at least about 8.6 mM $NaHCO_3$; at least about 8.8 mM $NaHCO_3$; at least about 9.0 mM $NaHCO_3$; at least about 10 mM $NaHCO_3$; at least about 20 mM $NaHCO_3$; at least about 30 mM $NaHCO_3$; at least about 40 mM $NaHCO_3$; at least about 50 mM $NaHCO_3$; at least about 60 mM $NaHCO_3$; at least about 70 mM $NaHCO_3$; at least about 80 mM $NaHCO_3$; at least about 90 mM $NaHCO_3$; at least about 100 mM $NaHCO_3$; at least about 200 mM $NaHCO_3$; at least about 300 mM $NaHCO_3$; at least about 400 mM $NaHCO_3$; at least about 500 mM $NaHCO_3$; at least about 600 mM $NaHCO_3$; at least about 700 mM $NaHCO_3$; at least about 800 mM $NaHCO_3$; at least about 900 mM $NaHCO_3$; or at least about 1000 mM $NaHCO_3$. It is understood that recitation of the above discrete values includes a range between each recited value.

As another example, a modified simulated body fluid can include about 0.4 mM $NaHCO_3$; about 0.6 mM $NaHCO_3$; about 0.8 mM $NaHCO_3$; about 1.0 mM $NaHCO_3$; about 1.2 mM $NaHCO_3$; about 1.4 mM $NaHCO_3$; about 1.6 mM $NaHCO_3$; about 1.8 mM $NaHCO_3$; about 2.0 mM $NaHCO_3$; about 2.2 mM $NaHCO_3$; about 2.4 mM $NaHCO_3$; about 2.6 mM $NaHCO_3$; about 2.8 mM $NaHCO_3$; about 3.0 mM $NaHCO_3$; about 3.2 mM $NaHCO_3$; about 3.4 mM $NaHCO_3$; about 3.6 mM $NaHCO_3$; about 3.8 mM $NaHCO_3$; about 4.0 mM $NaHCO_3$; about 4.2 mM $NaHCO_3$; about 4.4 mM $NaHCO_3$; about 4.6 mM $NaHCO_3$; about 4.8 mM $NaHCO_3$; about 5.0 mM $NaHCO_3$; about 5.2 mM $NaHCO_3$; about 5.4 mM $NaHCO_3$; about 5.6 mM $NaHCO_3$; about 5.8 mM $NaHCO_3$; about 6.0 mM $NaHCO_3$; about 6.2 mM $NaHCO_3$; about 6.4 mM $NaHCO_3$; about 6.6 mM $NaHCO_3$; about 6.8 mM $NaHCO_3$; about 7.0 mM $NaHCO_3$; about 7.2 mM $NaHCO_3$; about 7.4 mM $NaHCO_3$; about 7.6 mM $NaHCO_3$; about 7.8 mM $NaHCO_3$; about 8.0 mM $NaHCO_3$; about 8.2 mM $NaHCO_3$; about 8.4 mM $NaHCO_3$; about 8.6 mM $NaHCO_3$; about 8.8 mM $NaHCO_3$; about 9.0 mM $NaHCO_3$; about 10 mM $NaHCO_3$; about 20 mM $NaHCO_3$; about 30 mM $NaHCO_3$; about 40 mM $NaHCO_3$; about 50 mM $NaHCO_3$; about 60 mM $NaHCO_3$; about 70 mM $NaHCO_3$; about 80 mM $NaHCO_3$; about 90 mM $NaHCO_3$; about 100 mM $NaHCO_3$; about 200 mM $NaHCO_3$; about 300 mM $NaHCO_3$; about 400 mM $NaHCO_3$; about 500 mM $NaHCO_3$; about 600 mM $NaHCO_3$; about 700 mM $NaHCO_3$; about 800 mM $NaHCO_3$; about 900 mM $NaHCO_3$; or about 1000 mM $NaHCO_3$. It is understood that recitation of the above discrete values includes a range between each recited value.

A modified simulated body fluid can include at least about 0.5 mM CaCl2). For example, a modified simulated body fluid can include at least about 0.5 mM CaCl2, at least about 1.0 mM $CaCl_2$), at least about 1.5 mM $CaCl_2$), at least about 2.0 mM $CaCl_2$), at least about 2.5 mM $CaCl_2$), at least about 3.0 mM $CaCl_2$), at least about 3.5 mM $CaCl_2$), at least about 4.0 mM $CaCl_2$), at least about 4.5 mM $CaCl_2$), at least about 5.0 mM $CaCl_2$), at least about 5.5 mM $CaCl_2$), at least about 6.0 mM $CaCl_2$), at least about 6.5 mM $CaCl_2$), at least about 7.0 mM $CaCl_2$), at least about 7.5 mM $CaCl_2$), at least about 8.0 mM $CaCl_2$), at least about 8.5 mM $CaCl_2$), at least about 9.0 mM $CaCl_2$), at least about 9.5 mM $CaCl_2$), at least about 10.0 mM $CaCl_2$), at least about 10.5 mM $CaCl_2$), at least about 11.0 mM $CaCl_2$), at least about 11.5 mM $CaCl_2$), at least about 12.0 mM $CaCl_2$), at least about 12.5 mM $CaCl_2$, at least about 13.0 mM $CaCl_2$, at least about 13.5 mM $CaCl_2$, at least about 14.0 mM $CaCl_2$, at least about 14.5 mM $CaCl_2$, at least about 15.0 mM $CaCl_2$, at least about 15.5 mM $CaCl_2$, at least about 16.0 mM $CaCl_2$, at least about 16.5 mM $CaCl_2$, at least about 17.0 mM $CaCl_2$, at least about 17.5 mM $CaCl_2$, at least about 18.0 mM $CaCl_2$, at least about 18.5 mM $CaCl_2$, at least about 19.0 mM $CaCl_2$, at least about 19.5 mM $CaCl_2$, at least about 20.0 mM $CaCl_2$, at least about 25 mM $CaCl_2$, at least about 30 mM $CaCl_2$, at least about 35 mM $CaCl_2$, at least about 40 mM $CaCl_2$, at least about 45 mM $CaCl_2$, or at least about 50 mM $CaCl_2$. It is understood that recitation of the above discrete values includes a range between each recited value.

As another example, a modified simulated body fluid can include about 0.5 mM $CaCl_2$, about 1.0 mM $CaCl_2$, about 1.5 mM $CaCl_2$, about 2.0 mM $CaCl_2$; about 2.5 mM $CaCl_2$, about 3.0 mM $CaCl_2$, about 3.5 mM $CaCl_2$, about 4.0 mM $CaCl_2$, about 4.5 mM $CaCl_2$, about 5.0 mM $CaCl_2$, about 5.5 mM $CaCl_2$, about 6.0 mM $CaCl_2$, about 6.5 mM $CaCl_2$, about 7.0 mM $CaCl_2$, about 7.5 mM $CaCl_2$; about 8.0 mM $CaCl_2$, about 8.5 mM $CaCl_2$, about 9.0 mM $CaCl_2$, about 9.5 mM $CaCl_2$, about 10.0 mM $CaCl_2$, about 10.5 mM $CaCl_2$, about 11.0 mM $CaCl_2$; about 11.5 mM $CaCl_2$, about 12.0 mM $CaCl_2$, about 12.5 mM $CaCl_2$, about 13.0 mM $CaCl_2$, about 13.5 mM $CaCl_2$, about 14.0 mM $CaCl_2$, about 14.5 mM $CaCl_2$; about 15.0 mM $CaCl_2$, about 15.5 mM $CaCl_2$, about 16.0 mM $CaCl_2$, about 16.5 mM $CaCl_2$, about 17.0 mM $CaCl_2$, about 17.5 mM $CaCl_2$, about 18.0 mM $CaCl_2$; about 18.5 mM $CaCl_2$, about 19.0 mM $CaCl_2$, about 19.5 mM $CaCl_2$, about 20.0 mM $CaCl_2$, about 25 mM $CaCl_2$, about 30 mM $CaCl_2$, about 35 mM $CaCl_2$, about 40 mM $CaCl_2$, about 45 mM $CaCl_2$, or about 50 mM $CaCl_2$. It is understood that recitation of the above discrete values includes a range between each recited value.

A modified simulated body fluid can include at least about 0.2 mM $KH_2PO_4$. For example, a modified simulated body fluid can include at least about 0.2 mM $KH_2PO_4$; at least about 0.4 mM $KH_2PO_4$; at least about 0.6 mM $KH_2PO_4$; at least about 0.8 mM $KH_2PO_4$; at least about 1.0 mM $KH_2PO_4$; at least about 1.2 mM $KH_2PO_4$; at least about 1.4 mM $KH_2PO_4$; at least about 1.6 mM $KH_2PO_4$; at least about 1.8 mM $KH_2PO_4$; at least about 2.0 mM $KH_2PO_4$; at least about 2.2 mM $KH_2PO_4$; at least about 2.4 mM $KH_2PO_4$; at least about 2.6 mM $KH_2PO_4$; at least about 2.8 mM $KH_2PO_4$; at least about 3.0 mM $KH_2PO_4$; at least about 3.2 mM $KH_2PO_4$; at least about 3.4 mM $KH_2PO_4$; at least about 3.6 mM $KH_2PO_4$; at least about 3.8 mM $KH_2PO_4$; at least about 4.0 mM $KH_2PO_4$; at least about 4.2 mM $KH_2PO_4$; at least about 4.4 mM $KH_2PO_4$; at least about 4.6 mM $KH_2PO_4$; at least about 4.8 mM $KH_2PO_4$; at least about 5.0 mM $KH_2PO_4$; at least about 5.2 mM $KH_2PO_4$; at least about 5.4 mM $KH_2PO_4$; at least about 5.6 mM $KH_2PO_4$; at least about 5.8 mM $KH_2PO_4$; at least about 6.0 mM $KH_2PO_4$; at least about 6.2 mM $KH_2PO_4$; at least about 6.4 mM $KH_2PO_4$; at least about 6.6 mM $KH_2PO_4$; at least about 6.8 mM $KH_2PO_4$; at least about 7.0 mM $KH_2PO_4$; at least about 7.2 mM $KH_2PO_4$; at least about 7.4 mM $KH_2PO_4$; at least about 7.6 mM $KH_2PO_4$; at least about 7.8 mM $KH_2PO_4$; at least about 8.0 mM $KH_2PO_4$; at least about 8.2 mM $KH_2PO_4$; at least about 8.4 mM $KH_2PO_4$; at least about 8.6 mM $KH_2PO_4$; at least about 8.8 mM $KH_2PO_4$; at least about 9.0 mM $KH_2PO_4$; at least about 9.2 mM $KH_2PO_4$; at least about 9.4 mM $KH_2PO_4$; at least about 9.6 mM $KH_2PO_4$; at least about 9.8 mM $KH_2PO_4$; at least about 10.0 mM $KH_2PO_4$; at least about 20 mM $KH_2PO_4$; at least about 30 mM $KH_2PO_4$; at least about 40 mM $KH_2PO_4$; at least about 50 mM $KH_2PO_4$; at least about 60 mM $KH_2PO_4$; at least about 70 mM $KH_2PO_4$; at least about 80 mM $KH_2PO_4$; at least about 90 mM $KH_2PO_4$; at least about 100 mM $KH_2PO_4$; at least about 110 mM $KH_2PO_4$; at least about 120 mM $KH_2PO_4$; at least about 130 mM $KH_2PO_4$; at least about 140 mM $KH_2PO_4$; at least about 150 mM $KH_2PO_4$; at least about 160 mM $KH_2PO_4$; at least about 170 mM $KH_2PO_4$; at least about 180 mM $KH_2PO_4$; at least about 190 mM $KH_2PO_4$; or at least about 200 mM $KH_2PO_4$. It is understood that recitation of the above discrete values includes a range between each recited value.

As another example, a modified simulated body fluid can include about 0.2 mM $KH_2PO_4$; about 0.4 mM $KH_2PO_4$; about 0.6 mM $KH_2PO_4$; about 0.8 mM $KH_2PO_4$; about 1.0 mM $KH_2PO_4$; about 1.2 mM $KH_2PO_4$; about 1.4 mM $KH_2PO_4$; about 1.6 mM $KH_2PO_4$; about 1.8 mM $KH_2PO_4$; about 2.0 mM $KH_2PO_4$; about 2.2 mM $KH_2PO_4$; about 2.4 mM $KH_2PO_4$; about 2.6 mM $KH_2PO_4$; about 2.8 mM $KH_2PO_4$; about 3.0 mM $KH_2PO_4$; about 3.2 mM $KH_2PO_4$; about 3.4 mM $KH_2PO_4$; about 3.6 mM $KH_2PO_4$; about 3.8 mM $KH_2PO_4$; about 4.0 mM $KH_2PO_4$; about 4.2 mM $KH_2PO_4$; about 4.4 mM $KH_2PO_4$; about 4.6 mM $KH_2PO_4$; about 4.8 mM $KH_2PO_4$; about 5.0 mM $KH_2PO_4$; about 5.2 mM $KH_2PO_4$; about 5.4 mM $KH_2PO_4$; about 5.6 mM $KH_2PO_4$; about 5.8 mM $KH_2PO_4$; about 6.0 mM $KH_2PO_4$; about 6.2 mM $KH_2PO_4$; about 6.4 mM $KH_2PO_4$; about 6.8 mM $KH_2PO_4$; about 7.0 mM $KH_2PO_4$; about 7.2 mM $KH_2PO_4$; about 7.4 mM $KH_2PO_4$; about 7.6 mM $KH_2PO_4$; about 7.8 mM $KH_2PO_4$; about 8.0 mM $KH_2PO_4$; about 8.2 mM $KH_2PO_4$; about 8.4 mM $KH_2PO_4$; about 8.6 mM $KH_2PO_4$; about 8.8 mM $KH_2PO_4$; about 9.0 mM $KH_2PO_4$; about 9.2 mM $KH_2PO_4$; about 9.4 mM $KH_2PO_4$; about 9.6 mM $KH_2PO_4$; about 9.8 mM $KH_2PO_4$; about 10.0 mM $KH_2PO_4$; about 20 mM $KH_2PO_4$; about 30 mM $KH_2PO_4$; about 40 mM $KH_2PO_4$; about 50 mM $KH_2PO_4$; about 60 mM $KH_2PO_4$; about 70 mM $KH_2PO_4$; about 80 mM $KH_2PO_4$; about 90 mM $KH_2PO_4$; about 100 mM $KH_2PO_4$; about 110 mM $KH_2PO_4$; about 120 mM $KH_2PO_4$; about 130 mM $KH_2PO_4$; about 140 mM $KH_2PO_4$; about 150 mM $KH_2PO_4$; about 160 mM $KH_2PO_4$; about 170 mM $KH_2PO_4$; about 180 mM $KH_2PO_4$; about 190 mM $KH_2PO_4$; or about 200 mM $KH_2PO_4$. It is understood that recitation of the above discrete values includes a range between each recited value.

In some embodiments, the solution can comprise a surfactant, which can change the morphology of the calcium-containing mineral layer. Any surfactant now known or later discovered may be used here. In some embodiments, the surfactant can be Tween 20™.

Coatings

Coating materials comprise various materials designed to be deposited on the surface of the bone materials. Exemplary methods for producing a primer coated scaffold (e.g., bone material) using a primer coating composition comprising a polymer are described herein. For example, the primer coating composition can be a solution comprising a polymer and a solvent. As another example, the primer coating composition can be any composition comprising a polymer. The primer coating composition can be in solution state, solid state, liquid state, gas state, plasma state, or vapor phase. As another example, the primer coating composition can be a powder.

As described herein, the composition of a polymer layer on a scaffold can be manipulated by adjusting the primer coating composition, such as the polymer composition (e.g., type, concentration), additives, or solvent composition (e.g., type, concentration) in the primer coating composition.

Polymers

Embodiments include exemplary methods for producing a primer coated scaffold using a polymer containing coating composition in solution. For example, a polymer containing primer coating composition can include any conventional polymer (see e.g., Nair, et al. Prog. Poly. Sci 2007 32(8-9) 762-798; Miller, Chou, et al. Prog. Poly. Sci 2003 28 1223-1270). As another example, a polymer in a polymer containing primer coating composition can include one or more of acrylic resin, alginate, caprolactone, collagen, chitosan, hyaluronic acid, hydrogel, hydroxybutyric acid, polyanhydride, polycaprolactone (PCL), poly(dimethylglycolic acid), polydioxanone (PDO), polyester, polyethylene, poly(ethylene glycol), poly(glycolide) (PGA), poly(glycolic acid), polyhydroxobutyrate, poly(2-hydroxyethyl-methacrylate), poly-lactide-co-glycolide (PLCG), poly(D,L-lactide-co-glycolide) (PLG), poly(lactide-co-glycolic acid) (PLGA), polylactide (PLA), polylactic acid (PLLA), poly-lactide-co-glycolide (PLCG), poly(methylethylglycolic acid), polymethylmethacrylate, polyphosphazenes, polyphosphoesters, polypropylene, poly(propylene fumarate), polyurethane (PU), silicone rubber, or combinations or copolymers thereof.

As another example, a polymer in a polymer containing primer coating can include one or more of a bioresorbable polyester or its copolymers. The biodegradable polyester or its copolymer can be, for example, one or more of the following: polycaprolactone (PCL), poly(D,L-lactide-co-glycolide) (PLG), polylactide (PLA), polylactic acid (PLLA), or poly-lactide-co-glycolide (FLCG).

The primer coating composition, as described herein, can include two polymers. For example, the polymer containing primer coating composition, as described herein, can comprise a ratio of two polymers of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, or about 1:40. It is understood that recitation of the above discrete values includes a range between each recited value.

The primer coating composition can include a powder comprising one or more polymers as described herein. The powder can comprise a range of particle grain sizes. The powder can comprise an average grain size. For example, the powder can include a grain size or an average grain size of about 1 μm to about 5,000 μm. As another example, the powder can include a grain size or an average grain size of about 10 μm to about 500 μm. As another example, the powder can include a grain size or an average grain size of about 1 μm; about 2 μm; about 3 μm; about 4 μm; about 5 μm; about 6 μm; about 7 μm; about 8 μm; about 9 μm; about 10 μm; about 11 μm; about 12 μm; about 13 μm; about 14 μm; about 15 μm; about 16 μm; about 17 μm; about 18 μm; about 19 μm; about 20 μm; about 21 μm; about 22 μm; about 23 μm; about 24 μm; about 25 μm; about 26 μm; about 27 μm; about 28 μm; about 29 μm; about 30 μm; about 31 μm; about 32 μm; about 33 μm; about 34 μm; about 35 μm; about 36 μm; about 37 μm; about 38 μm; about 39 μm; about 40 μm; about 41 μm; about 42 μm; about 43 μm; about 44 μm; about 45 μm; about 46 μm; about 47 μm; about 48 μm; about 49 μm; about 50 μm; about 60 μm; about 70 μm; about 80 μm; about 90 μm; about 100 μm; about 110 μm; about 120 μm; about 130 μm; about 140 μm; about 150 μm; about 160 μm; about 170 μm; about 180 μm; about 190 μm; about 200 μm; about 210 μm; about 220 μm; about 230 μm; about 240 μm; about 250 μm; about 260 μm; about 270 μm; about 280 μm; about 290 μm; about 300 μm; about 310 μm; about 320 μm; about 330 μm; about 340 μm; about 350 μm; about 360 μm; about 370 μm; about 380 μm; about 390 μm; about 400 μm; about 410 μm; about 420 μm; about 430 μm; about 440 μm; about 450 μm; about 460 μm; about 470 μm; about 480 μm; about 490 μm; or about 500 μm. It is understood that recitation of the above discrete values includes a range between each recited value.

Solvents

In some embodiments, there are exemplary methods for producing a primer coated scaffold (bone material) using a polymer containing coating composition in solution (e.g., primer coating solution). For example, the polymer containing primer coating solution can include any conventional solvent (see e.g., Nair et al. Prog. Poly. Sci 2007 32(8-9) 762-798; Miller Chou et al. Prog. Poly. Sci 2003 28 1223-1270). As another example, the solvent can be sufficient for polymer dissolution (see e.g., Miller-Chou et al. 2003 Prog. Polym. Sci. (28) 1223-1270). As another example, the solvent in the polymer containing primer coating solution can include one or more of acetic acid, alcohols, aliphatic ethers, aniline, aromatic hydrocarbons, chlorinated hydrocarbons, aromatic hydrocarbons, aqueous alkali, aqueous solutions of cupriethylenediamine, benzene, biphenyl, chlorinated aliphatic hydrocarbons, chlorinated hydrocarbons, chloroform, chlorophenol, chlorobenzene, cyclohexanone, chlorinated hydrocarbons, chloroauric acid, DCM, dimethylformamide (DMF), DMSO, dichlorobiphenyl, dioxane, dilute aqueous sodium hydroxide, 1,2-dichlorobenzene, dichloromethane, DCM, ethanol, ethyl acetate, ethylene carbonate, esters, formic acid, glycols, halogenated hydrocarbons, HFIP, higher aliphatic esters or ketones, halogenated hydrocarbons, higher aliphatic esters, higher aliphatic ketones, ketones, higher ketones, hydrocarbons, isopropylamine, methyl ethyl ketone, morpholine, methylene chloride, methanol, methyl ethyl ketone, m-Cresol, NMP, phenol, phenylenediamines, sulfuric acid, tetramethylurea, toluene, trifluoroacetic acid, THD, tetramethylurea, tetrahydrofuran (THF), trifluoroacetic acid, trichloroethanol, Toluene, trichloroethane, trichloroacetaldehyde hydrate, perfluorokerosene, pyridine, phenyl ether, piperazine, pyridine, water, or xylene, or combinations thereof.

The polymer containing primer coating solution, as described herein, can include two solvents. For example, the polymer containing primer coating solution, as described herein, can include a ratio of two solvents of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, or about 1:40. It is understood that recitation of the above discrete values includes a range between each recited value.

The polymer containing primer coating solution, as described herein, can have a weight % of polymer/volume of solvent (% w/v). For example, the polymer containing primer coating solution, as described herein, can have about 0.1% weight polymer/volume of solvent; about 0.2,% weight polymer/volume of solvent; about 0.3% weight polymer/volume of solvent; about 0.4% weight polymer/volume of solvent; about 0.5% weight polymer/volume of solvent; about 0.6% weight polymer/volume of solvent; about 0.7% weight polymer/volume of solvent; about 0.8% weight polymer/volume of solvent; about 0.9% weight polymer/volume of solvent; about 1% weight polymer/volume of solvent; about 2% weight polymer/volume of solvent; about 3% weight polymer/volume of solvent; about 4% weight polymer/volume of solvent; about 5% weight polymer/volume of solvent; about 6% weight polymer/volume of solvent; about 7% weight polymer/volume of solvent; about 8% weight polymer/volume of solvent; about 9% weight polymer/volume of solvent; about 10% weight polymer/volume of solvent; 11% weight polymer/volume of solvent; about 12% weight polymer/volume of solvent; about 13% weight polymer/volume of solvent; about 14% weight polymer/volume of solvent; about 15% weight polymer/volume of solvent; about 16% weight polymer/volume of solvent; about 17% weight polymer/volume of solvent; about 18% weight polymer/volume of solvent; about 19% weight polymer/volume of solvent; about 20% weight polymer/volume of solvent; 21% weight polymer/volume of solvent; about 22% weight polymer/volume of solvent; about 23% weight polymer/volume of solvent; about 24% weight polymer/volume of solvent; about 25% weight polymer/volume of solvent; about 26% weight polymer/volume of solvent; about 27% weight polymer/volume of solvent; about 28% weight polymer/volume of solvent; about 29% weight polymer/volume of solvent; about 30% weight polymer/volume of solvent; 31% weight polymer/volume of solvent; about 32% weight polymer/volume of solvent; about 33% weight polymer/volume of solvent; about 34% weight polymer/volume of solvent; about 35% weight polymer/volume of solvent; about 36% weight polymer/volume of solvent; about 37% weight polymer/volume of solvent; about 38% weight polymer/volume of solvent; about 39% weight polymer/volume of solvent; about 40% weight polymer/volume of solvent; 41% weight polymer/volume of solvent; about 42% weight polymer/volume of solvent; about 43% weight polymer/volume of solvent; about 44% weight polymer/volume of solvent; about 45% weight polymer/volume of solvent; about 46% weight polymer/volume of solvent; about 47% weight polymer/volume of solvent; about 48% weight polymer/volume of solvent; about 49% weight polymer/volume of solvent; about 50% weight polymer/volume of solvent; about 60% weight polymer/volume of solvent; about 70% weight polymer/volume of solvent; about 80% weight polymer/volume of solvent; about 90% weight polymer/volume of solvent; or about 100% weight polymer/volume of solvent. It is understood that recitation of the above discrete values includes a range between each recited value.

A useful mineral coating can be prepared as described in U.S. application Ser. No. 15/060,547 filed Mar. 3, 2016 and published as US 20160271296 A1 and U.S. application Ser. No. 13/879,178 filed Sep. 25, 2009 and published as US 20140161886 A1. These entire disclosures are incorporated herein by reference in their entireties and provide mineral coatings having a plate-like nanostructure to an implant having macro surface markers (e.g., recesses and/or projections). In some embodiments, the plate-like nanostructure comprises nanoparticles having a size range from about 100 to about 200 nanometers.

As described in these patent applications, the mineral coating can be calcium-containing. For example, the calcium-containing mineral coating can include hydroxyapatite (HAP), α-tricalcium phosphate (α-TCP), β-tricalcium phosphate (β-TCP), amorphous calcium phosphate, dicalcium phosphate, octacalcium phosphate, calcium phosphate (CaP), or calcium carbonate. The calcium-containing mineral coating can comprise a plurality of layers, e.g., separate layers having distinct dissolution profiles. Under physiological conditions, solubility of calcium phosphate species can adhere to the following trend: amorphous calcium phosphate>dicalcium phosphate>octacalcium phosphate>β-TCP>HAP. A dicalcium phosphate mineral can have a dissolution rate that is more than fifty times higher than that of HAP. Therefore, creation of a matrix with distinct calcium phosphate layers allows for a broad range of dissolution patterns.

Although the invention has been described with reference to preferred embodiments, persons skilled in the art will recognize that changes may be made in form and detail without departing from the spirit and scope of the invention.

What is claimed is:

1. A method of identifying a coating on a bone material, the method comprising providing the bone material and a scanning device; adjusting a distance between the bone material and the scanning device; scanning the bone material using the scanning device;

and transmitting a scanned data from the scanning device to a processor configured to analyze the scanned data, and display the analyzed scanned data to identify the coating on the bone material based on the scanned data, the scanned data comprising an absorbance value when the coating meets or fails to meet a predetermined parameter, wherein the predetermined parameter comprises a coating distribution on the bone material, coating thickness on the bone material, coating nanometer structure on the bone material, coating color on the bone material, homogeneity of the coating on the bone material, phase of the coating on the bone material, coating composition on the bone material or a combination thereof, and the coating nanostructure comprises a plate-like nanostructure of carbonate substituted, calcium-deficient hydroxyapatite.

2. The method of claim 1, wherein (i) the method further comprises storing the identification of the coating in a database.

3. The method of claim 1, wherein the method further comprises marking the identification of the coating on the bone material.

4. The method of claim 1, wherein the bone material comprises a unique identifier.

5. The method of claim 4, wherein the unique identifier is part of a blockchain system generated by a database that represents unique information, data or characteristics about the bone material.

6. The method of claim 1, wherein the scanning device is a handheld spectrophotometer.

7. The method of claim 1, wherein the method comprises adjusting an angle between the bone material and the scanning device.

8. The method of claim 1, wherein the distance is adjusted manually by a user.

9. The method of claim 1, wherein the method comprises repeating the scanning of the bone material.

10. The method of claim 1, wherein the step of analyzing the scanned data comprises evaluating an optical information of the scanned data.

11. The method of claim 1, wherein the method comprises repeating the scanning of the bone material.

12. A method of identifying a coating on a bone material, the method comprising providing the bone material having a unique identifier; providing a spectrophotometer; adjusting a distance between the bone material and the spectrophotometer; scanning the bone material using the spectrophotometer; and transmitting a scanned data from the spectrophotometer to a processor configured to analyze the scanned data, and display the analyzed scanned data to identify the coating on the bone material based on the scanned data, the scanned data comprising an absorbance value when the coating meets or fails to meet a predetermined parameter, wherein the predetermined parameter comprises a coating distribution on the bone material, coating thickness on the bone material, coating nanometer structure on the bone material, coating color on the bone material, homogeneity of the coating on the bone material, phase of the coating on the bone material, coating composition on the bone material or a combination thereof, and the coating nanostructure comprises a plate-like nanostructure of carbonate substituted, calcium-deficient hydroxyapatite.

13. The method of claim 12, wherein the method further comprises storing the identification of the coating in a database.

14. The method of claim 12, wherein the method further comprises marking the identification of the coating on the bone material.

15. The method of claim 14, wherein the marking is 3D printed, lasered, stamped, or a combination thereof on the bone material.

16. The method of claim 12, wherein the unique identifier comprises a blockchain structure generated by a database that represents unique information, data or characteristics about the bone material.

17. The method of claim 12, wherein information associated with the unique identifier is encrypted.

18. A system for identifying a coating on a bone material, the system comprising a scanning device configured to scan the bone material, the scanning device configured to transmit data to a processor, the processor having logic to cause a computer to receive the scanned data, analyze the scanned data and display a coating status of the bone material based on the analyzed data, the analyzed data comprising an absorbance value when the coating status meets or fails to meet a predetermined parameter, wherein the predetermined parameter comprises a coating distribution on the bone material, coating thickness on the bone material, coating nanometer structure on the bone material, coating color on the bone material, homogeneity of the coating on the bone material, phase of the coating on the bone material, coating composition on the bone material or a combination thereof, and the coating nanostructure comprises a plate-like nanostructure of carbonate substituted, calcium-deficient hydroxyapatite.

* * * * *